(12) United States Patent
Shito

(10) Patent No.: US 10,213,518 B2
(45) Date of Patent: Feb. 26, 2019

(54) LIGHT ILLUMINATING APPARATUS

(71) Applicant: HOYA CANDEO OPTRONICS CORPORATION, Toda-shi, Saitama (JP)

(72) Inventor: Kazutaka Shito, Toda (JP)

(73) Assignee: HOYA CANDEO OPTRONICS CORPORATION, Toda-Shi, Saitama (JP)

( * ) Notice: Subject to any disclaimer, the term of this patent is extended or adjusted under 35 U.S.C. 154(b) by 0 days.

(21) Appl. No.: 15/400,309

(22) Filed: Jan. 6, 2017

(65) Prior Publication Data

US 2017/0197001 A1 Jul. 13, 2017

(30) Foreign Application Priority Data

Jan. 10, 2016 (JP) .................................. 2016-003105

(51) Int. Cl.
*A61L 2/10* (2006.01)
*G21K 5/00* (2006.01)
*G02B 6/44* (2006.01)
*G02B 6/02* (2006.01)

(52) U.S. Cl.
CPC ............ *A61L 2/10* (2013.01); *G02B 6/02395* (2013.01); *G02B 6/4401* (2013.01); *G21K 5/00* (2013.01)

(58) Field of Classification Search
USPC ...................................................... 250/432 R
See application file for complete search history.

(56) References Cited

U.S. PATENT DOCUMENTS

| 6,657,206 B2 * | 12/2003 | Keogh | H01J 65/044 |
| | | | 250/504 R |
| 8,587,451 B2 * | 11/2013 | Chen | G02B 17/0615 |
| | | | 340/815.4 |
| 9,093,258 B2 * | 7/2015 | Stibich | A61L 2/10 |

(Continued)

FOREIGN PATENT DOCUMENTS

| JP | H05254894 A | 10/1993 |
| JP | H07-72358 A | 3/1995 |

(Continued)

OTHER PUBLICATIONS

Taiwanese Office Action dated Dec. 28, 2017.
Foreign Office Action dated Nov. 22, 2017, with an English translation.

*Primary Examiner* — Phillip A Johnston
(74) *Attorney, Agent, or Firm* — Rabin & Berdo, P.C.

(57) ABSTRACT

Provided is a light illuminating apparatus irradiates a target object relatively moveable along a first direction with light. The apparatus includes a light source having a plurality of solid-state devices which irradiates the target object with the light in a second direction perpendicular to the first direction; a first reflecting part having at least one first reflecting surface placed at a downstream side in the second direction below the target object when viewed from the first direction, wherein the first reflecting part reflects a portion of the light from the light source incident on the first reflecting surface onto the target object; and a second reflecting part having a pair of second reflecting surfaces standing erect from the light source toward the first reflecting surface, wherein the second reflecting part guides the light from the light source into the first reflecting surface.

20 Claims, 28 Drawing Sheets

(56) References Cited

U.S. PATENT DOCUMENTS

| | | | |
|---|---|---|---|
| 9,302,460 B2* | 4/2016 | Chen | B33Y 30/00 |
| 9,370,046 B2* | 6/2016 | Childers | H05B 3/0038 |
| 9,592,156 B2* | 3/2017 | Huang | A61F 9/00804 |
| 2002/0050575 A1 | 5/2002 | Keogh et al. | |
| 2002/0106173 A1 | 8/2002 | Stupak et al. | |
| 2003/0053770 A1 | 3/2003 | Noddings et al. | |
| 2004/0032034 A1 | 2/2004 | Bhat | |
| 2011/0147356 A1 | 6/2011 | Leonhardt et al. | |
| 2013/0068969 A1 | 3/2013 | Childers | |
| 2015/0028020 A1 | 1/2015 | Childers | |

FOREIGN PATENT DOCUMENTS

| | | |
|---|---|---|
| JP | H10-005667 A | 1/1998 |
| JP | 2002-260595 A | 9/2002 |
| JP | 2016-210668 A | 12/2016 |
| TW | 2008-42513 A | 11/2008 |
| WO | WO-2015/013309 A1 | 1/2015 |

* cited by examiner

LIGHT ILLUMINATING APPARATUS

TECHNICAL FIELD

The present disclosure relates to a light illuminating apparatus for performing light irradiation on a target object which is relatively moveable along a predetermined direction, for example, an apparatus for curing a coating agent coated on an optical fiber.

BACKGROUND ART

In conventional process for optical fiber fabrication, to protect the surface of an optical fiber pulled out as a string and maintain the strength of the optical fiber, an ultraviolet curable coating agent is coated on the surface of the optical fiber. The coating agent is coated in uncured state by a coating apparatus, and is cured by a light illuminating apparatus that performs ultraviolet light irradiation (for example, Patent Literature 1).

Patent Literature 1 discloses an apparatus that allows an optical fiber pulled out as a string coated with a coating material (a coating agent) to pass through a curing chamber with an elliptical housing so as to cure the coating material. Inside the elliptical housing, an elliptical mirror, and a quartz halogen lamp extending parallel to the path of the optical fiber are installed, and the quartz halogen lamp and the optical fiber are respectively positioned at a first focal point and a second focal point of the elliptical mirror, to make sure that ultraviolet light irradiated from the quartz halogen lamp reaches the outer periphery of the optical fiber.

RELATED LITERATURES

Patent Literature

Japanese Patent Publication No. 7-72358

Non-Patent Literature

DISCLOSURE

Technical Problem

According to the apparatus disclosed by Patent Literature 1, ultraviolet light from the quartz halogen lamp or a discharge lamp positioned at the first focal point of the elliptical mirror reflects off the elliptical mirror, and then is properly guided into the optical fiber positioned at the second focal point of the elliptical mirror.

However, in the apparatus disclosed by Patent Literature 1, due to the need to focus light radiating in 360° from a bright point of the discharge lamp into the optical fiber, it is necessary to install the elliptical mirror to surround the discharge lamp and the optical fiber, and because a predetermined distance needs to be provided between the first focal point and the second focal point of the elliptical mirror, there is a problem with an increased overall size of the apparatus.

In this context, the present disclosure is designed to solve the problem, and therefore the present disclosure is directed to providing a small-sized light illuminating apparatus that can allow approximately uniform light irradiation onto the outer periphery of a target object such as an optical fiber, without using an elliptical mirror.

Technical Solution

To achieve the objective, a light illuminating apparatus of the present disclosure is a light illuminating apparatus that irradiates a target object relatively moveable along a first direction with light, and includes a light source having a plurality of solid-state devices which irradiates the target object with the light in a second direction perpendicular to the first direction; a first reflecting part having at least one first reflecting surface placed at a downstream side in the second direction below the target object when viewed from the first direction, wherein the first reflecting part reflects a portion of the light from the light source incident on the first reflecting surface onto the target object; and a second reflecting part having a pair of second reflecting surfaces standing erect from the light source toward the first reflecting surface, wherein the second reflecting part guides the light from the light source into the first reflecting surface.

According to this configuration, because light from the light source directly irradiates the side of the target object facing the light source and reflected light from the first reflecting part irradiates the side of the target object facing away from the light source, the outer periphery of the target object can be surely irradiated with light. Furthermore, because a solid-state device which emits light spreading in 180° was applied as a light source, the need to use an elliptical mirror as conventional is eliminated, and the light source and the target object can be placed at a smaller distance therebetween than prior art, thereby achieving miniaturization of the light illuminating apparatus. Furthermore, because a solid-state device with no hot wire can be applied as a light source, a temperature rise of the target object can be prevented as compared to a traditional configuration using a discharge lamp. Furthermore, because a temperature rise of the light illuminating apparatus itself is prevented, a fan for cooling the light illuminating apparatus can be also reduced in size, making it possible to further reduce the size of the light illuminating apparatus itself.

Furthermore, the first reflecting surface preferably has line symmetry with respect to a normal line passing through a center of the light source when viewed from the first direction. Furthermore, in this case, preferably, the first reflecting surface is a plane and at least two in number, and when viewed from the first direction, normal lines of at least two first reflecting surfaces are arranged to pass through a point on the normal line passing through the center of the light source. Furthermore, in this case, preferably, the first reflecting surface may be equivalent to a side of a polygon having an inner center on a point on the normal line passing through the center of the light source when viewed from the first direction. Furthermore, the polygon is preferably a polygon including a triangle up to an octadecagon. Furthermore, the target object may be placed in a space between the inner center and the first reflecting surface.

Furthermore, the first reflecting surface may be in a shape of a semicircle having a center disposed on the normal line passing through the center of the light source when viewed from the first direction, and the target object may be placed in a space between the center of the semicircle and the first reflecting surface.

Furthermore, the pair of second reflecting surfaces may be respectively parallel to the second direction when viewed from the first direction.

Furthermore, the pair of second reflecting surfaces may be inclined to the second direction when viewed from the first direction, and a spacing of the pair of second reflecting surfaces may be narrower as it goes farther from the light source.

Furthermore, when a maximum intensity of the light on an outer peripheral surface of the target object is MAX and a minimum intensity is MIN, preferably, the following equation (1) is satisfied:

$$MIN/MAX \geq 30\% \quad (1)$$

Furthermore, the light illuminating apparatus may include a heat radiation member which is thermally joined to the first reflecting part and the second reflecting part, and configured to radiate heat from the first reflecting part and the second reflecting part. Furthermore, in this case, preferably, the heat radiation member is in a shape of a plate, and has a receiving part on one side surface thereof to receive the first reflecting part and the second reflecting part. Furthermore, in this case, the heat radiation member preferably has a plurality of heat radiation fins on the other side surface opposite to the one side surface. Furthermore, in this case, a cooling fan is preferably provided to blow air to the heat radiation fins.

Furthermore, the light illuminating apparatus may further include a light transmitting pipe installed extending in the first direction to cover the target object, the light transmitting pipe through which the light from the light source transmits.

Furthermore, the light is preferably light in ultraviolet wavelength range.

Furthermore, the target object may have a shape of a line, a sphere or a particle, and the light in ultraviolet wavelength range may cure a coating agent coated on the outer peripheral surface of the target object.

Furthermore, the target object may be in liquid phase, and the light in ultraviolet wavelength range may sterilize the target object.

Advantageous Effects

According to the present disclosure as described above, it is possible to realize a small-sized light illuminating apparatus that can allow approximately uniform light irradiation onto the outer periphery of a target object such as an optical fiber, without using an elliptical mirror.

Figure 1:
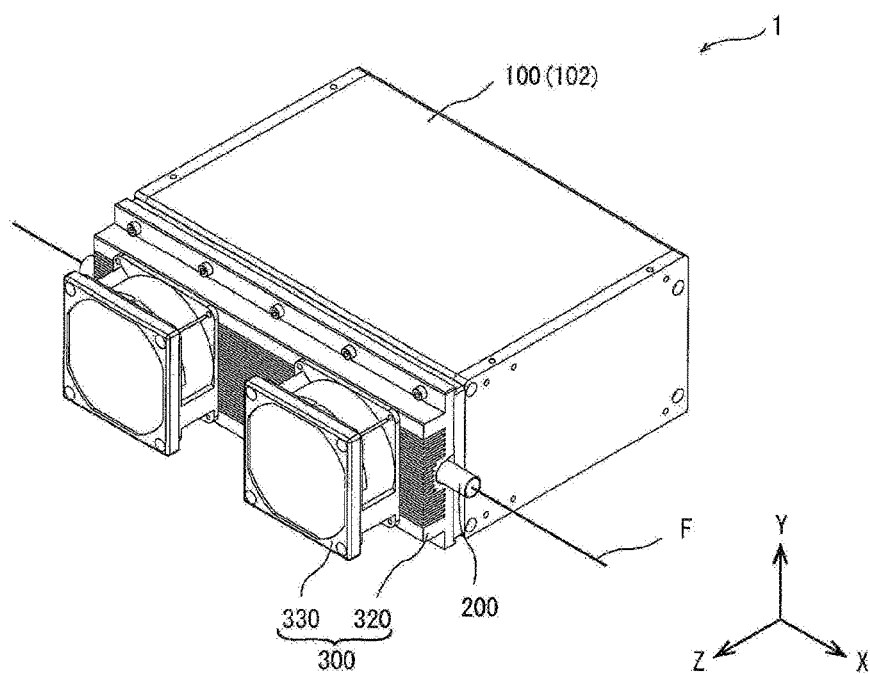
FIG. 1 is an exterior perspective view illustrating a configuration of a light illuminating apparatus according to a first embodiment of the present disclosure.

DETAILED DESCRIPTION OF MAIN ELEMENTS 1, 2 . . . Light illuminating apparatus
100 . . . Light source unit
102 . . . Case
102a . . . Front panel
102b . . . Opening
104 . . . Window
110 . . . LED module
111 . . . Inner reflecting mirror
113 . . . Substrate
115 . . . LED device
200, 200M . . . Light transmitting pipe
300 . . . Mirror module
310, 310A, 310B, 310C, 310D, 310E, 310F, 310G, 310H . . . Reflecting mirror
311 . . . First reflecting part
311a, 311Aa, 311Ba, 3110a, 311Da, 311Ea, 312Fa . . . First reflecting surface
312 . . . Second reflecting part
312a, 312Ga, 312Ha . . . Second reflecting surface
320 . . . Mirror frame
322 . . . Concave part
324 . . . Heat radiation fin
330 . . . Cooling fan

MODE FOR INVENTION

Hereinafter, the embodiments of the present disclosure will be described in detail with reference to the accompanying drawings. Furthermore, in the drawings, like or equivalent parts are given like reference symbols, and its description is not repeated.

First Embodiment

Figure 2:
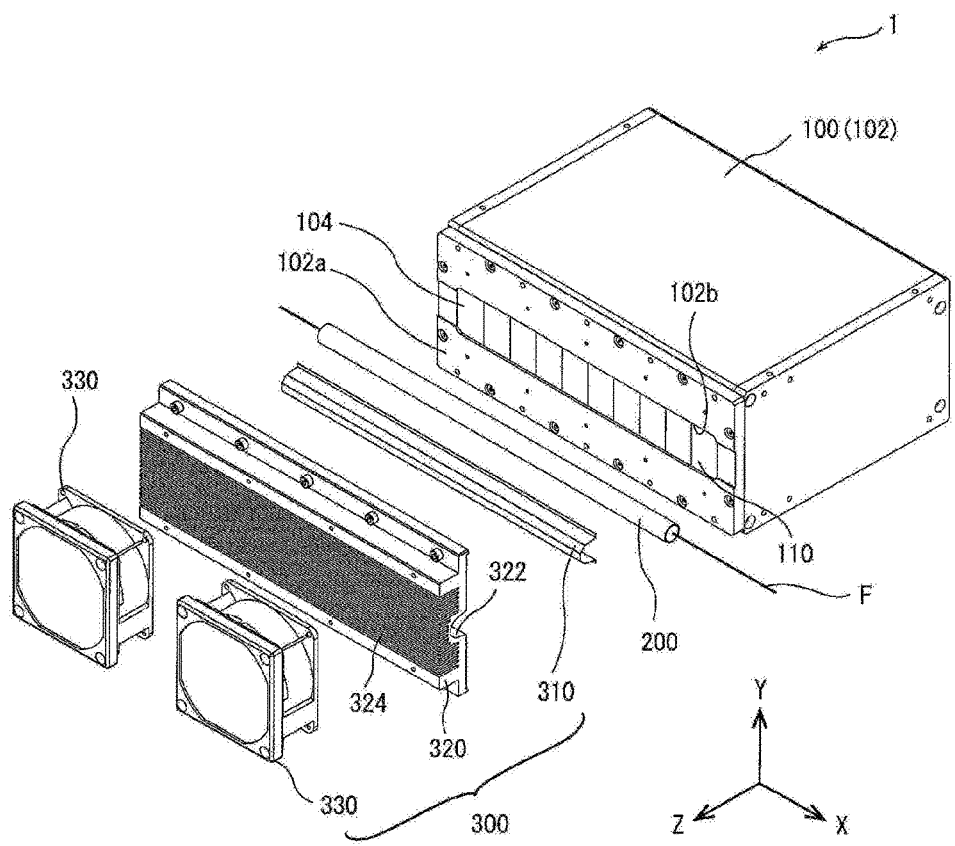
FIG. 2 is an exploded perspective view of the light illuminating apparatus of FIG. 1.

FIG. 1 is an exterior perspective view illustrating a configuration of a light illuminating apparatus 1 according to a first embodiment of the present disclosure. Furthermore, FIG. 2 is an exploded perspective view of the light illuminating apparatus 1. The light illuminating apparatus 1 of this embodiment is a light source apparatus for curing a coating agent coated on an optical fiber F pulled out as a string, and emits ultraviolet ray of a line shape along the optical fiber F moving (traveling) in one direction. Furthermore, in the specification, as shown in the coordinates of FIG. 1, the movement direction of the optical fiber F is defined as an X-axis direction, a direction in which a light emitting diode (LED) device 115 (a solid-state device) as described below emits ultraviolet light is defined as a Z-axis direction, and a direction perpendicular to the X-axis direction and the Z-axis direction is defined as a Y-axis direction.

As shown in FIGS. 1 and 2, the light illuminating apparatus 1 of this embodiment has a light source unit 100, a light transmitting pipe 200, and a mirror module 300.

The light source unit 100 has a box-shaped case 102 where a plurality of LED modules 110 is received inside. Furthermore, a front panel 102a of the case 102 (a cross section in the Z-axis direction) has a rectangular opening 102b, and a window 104 made of glass on its inner side, through which ultraviolet light emits.

Figure 3:
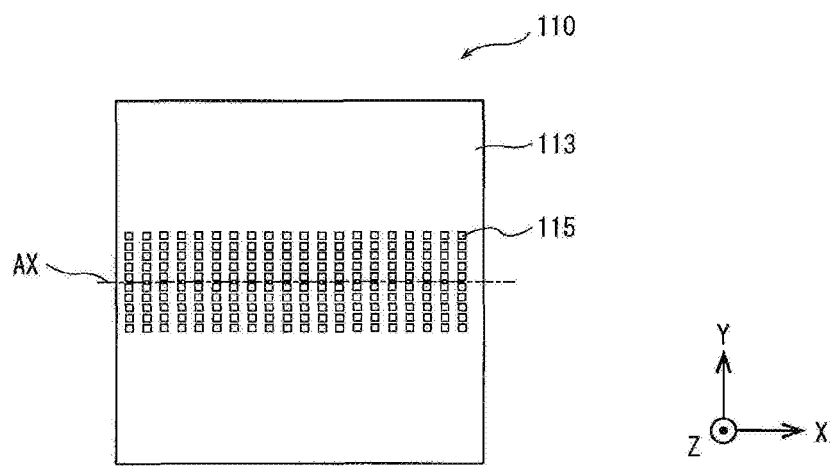
FIG. 3 is a front view showing a configuration of a light emitting diode (LED) module provided in the light illuminating apparatus according to the first embodiment of the present disclosure.
Figure 4:
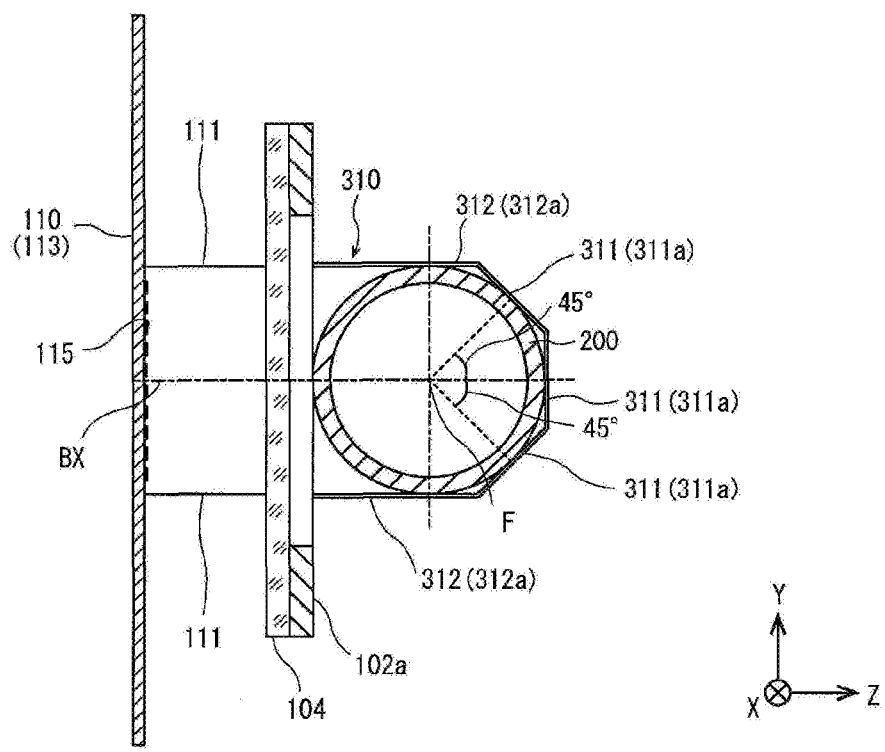
FIG. 4 is a cross-sectional view of the Y-Z plane illustrating a positional relationship between the LED module, a window, a light transmitting pipe, and a reflecting mirror provided in the light illuminating apparatus according to the first embodiment of the present disclosure.

FIG. 3 is a front view showing a configuration of the LED module 110 of this embodiment. Furthermore, FIG. 4 is a cross-sectional view of the Y-Z plane illustrating a positional relationship between the LED module 110, the window 104, the light transmitting pipe 200, and a reflecting mirror 310 of the mirror module 300. As shown in FIG. 3, the LED module 110 includes a substrate 113 of a rectangular shape parallel to the X-axis direction and the Y-axis direction, and 200 LED devices 115 placed on the substrate 113 in the arrangement of 10 rows (Y-axis direction)×20 (X-axis direction).

The 200 LED devices 115 of the LED module 110 are arranged on the surface of the substrate 113 with an optical axis aligned in the Z-axis direction. The substrate 113 has an anode pattern (not shown) and a cathode pattern (not shown) thereon to supply power to each LED device 115, and each LED device 115 is respectively soldered and electrically connected to the anode pattern and the cathode pattern.

Furthermore, the substrate 113 is electrically connected to a driver circuit not shown with a wiring cable not shown, to allow each LED device 115 to be supplied with driving power from the driver circuit through the anode pattern and the cathode pattern. When driving power is supplied to each LED device 115, ultraviolet light emits from each LED device 115 in an amount of light in proportion to driving current (for example, 385 nm wavelength), and ultraviolet light of a line shape parallel to the X-axis direction emits from the LED module 110. As shown in FIG. 2, in this embodiment, 10 LED modules 110 are arranged in the X-axis direction, and are configured such that ultraviolet light of a line shape from each LED module 110 continue to run in the X-axis direction. Furthermore, driving current supplied to each LED device 115 of this embodiment is adjusted so that each LED device 115 emits ultraviolet light in an approximately uniform amount of light, and ultraviolet light of a line shape emitting from the light source unit 100 has an approximately uniform light amount distribution in the X-axis direction and Y-axis direction. Furthermore, as shown in FIG. 4, the light source unit 100 of this embodiment has a pair of inner reflecting mirrors 111 that extends straight in the X-axis direction between the LED module 110 and the window 104 and is parallel to the Z-axis direction to guide ultraviolet light of a line shape from the LED module 110 in the Z-axis direction. Furthermore, in the specification, for convenience of description, as shown in FIG. 3, a straight line that divides an area where 200 LED devices 115 are arranged into two in the Y-axis direction is defined as a straight line AX, and a straight line perpendicular to the straight line AX and parallel to the Z-axis direction is defined as a straight line BX (a normal line passing through the center of the light source) (FIG. 4).

The light transmitting pipe 200 is, for example, a pipe made of quartz glass having an outer diameter of φ 20 mm and an inner diameter of φ 17 mm, through which ultraviolet light from the light source unit 100 can transmit, and the light transmitting pipe 200 is placed between the window 104 and the mirror module 300, extending in the X-axis direction, and is fixed by a support member not shown at two ends in the X-axis direction (FIGS. 1, 2, and 4). Furthermore, the optical fiber F moving in the X-axis direction is inserted into and passes through the light transmitting pipe 200. Furthermore, for example, the optical fiber F of this embodiment has an outer diameter of φ 0.25 mm, is placed along the center axis of the light transmitting pipe 200, and is allowed to move at the rate of 200-1200 m/min in the X-axis direction.

As shown in FIGS. 1 and 2, the mirror module 300 includes a reflecting mirror 310, a mirror frame 320, and a cooling fan 330.

The reflecting mirror 310 is a member that extends in the X-axis direction to cover the light transmitting pipe 200, and is placed on the front surface of the case 102 (FIG. 4). For example, the reflecting mirror 310 is formed by bending an elongated plate of aluminum along the X-axis direction, and has a plurality of reflecting surfaces (a first reflecting surface 311a of a first reflecting part 311 and a second reflecting surface 312a of a second reflecting part 312 as described below) on the side facing the light transmitting pipe 200.

As shown in FIG. 4, the reflecting mirror 310 of this embodiment is a member that reflects ultraviolet light emitting from the light source unit 100 onto the optical fiber F, and the reflecting mirror 310 is bent in four places along the X-axis direction so that its cross section has a roughly U shape, and includes a first reflecting part 311 and a second reflecting part 312.

The second reflecting part 312 stands erect in the Z-direction from the window 104 of the light source unit 100, and includes a pair of second reflecting surfaces 312a parallel to the Z-axis direction to guide ultraviolet light emitting from the window 104 into a first reflecting surface 311a of the first reflecting part 311. Furthermore, as shown in FIG. 4, in this embodiment, a spacing of the pair of second reflecting surfaces 312a is, for example, 20 mm, and is set to be approximately equal to a spacing of the pair of inner reflecting mirrors 111.

The first reflecting part 311 includes three first reflecting surfaces 311a arranged at the downstream side in the Z-axis direction below the optical fiber F, and is configured to reflect a portion of ultraviolet light incident on each first reflecting surface 311a to onto the other side of the outer peripheral surface of the optical fiber F (an area of half of the outer peripheral surface disposed at the downstream side in the Z-axis direction). Furthermore, as shown in FIG. 4, each first reflecting surface 311a of this embodiment is installed such that normal lines passing through the center of each first reflecting surface 311a pass through the center axis (i.e., the optical fiber F) of the light transmitting pipe 200 and are arranged at an angular interval of 45° around the optical fiber F. That is, each first reflecting part 311 of this embodiment is equivalent to one side of a regular octagon with the optical fiber F serving as an inner center, and is line-symmetric with respect to the straight line BX.

Figure 5A:
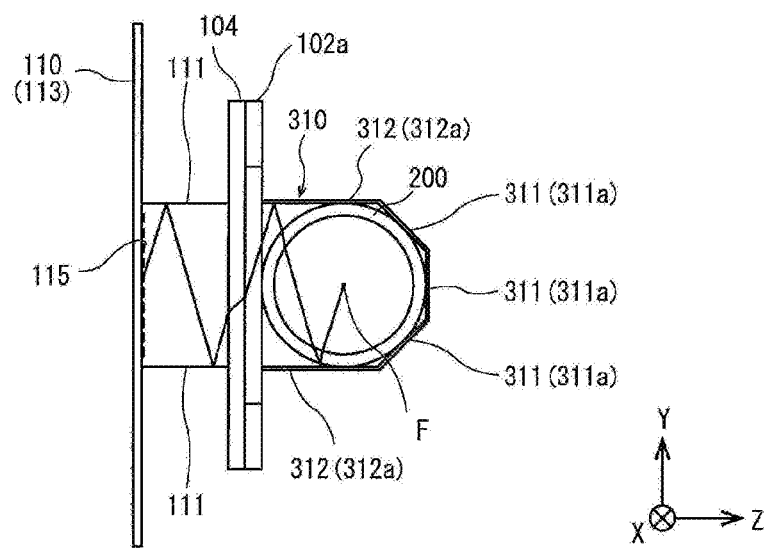
FIG. 5A and FIG. 5B are respectively a light ray diagram of ultraviolet light emitting from a light source unit of the light illuminating apparatus according to the first embodiment of the present disclosure.
Figure 5B:
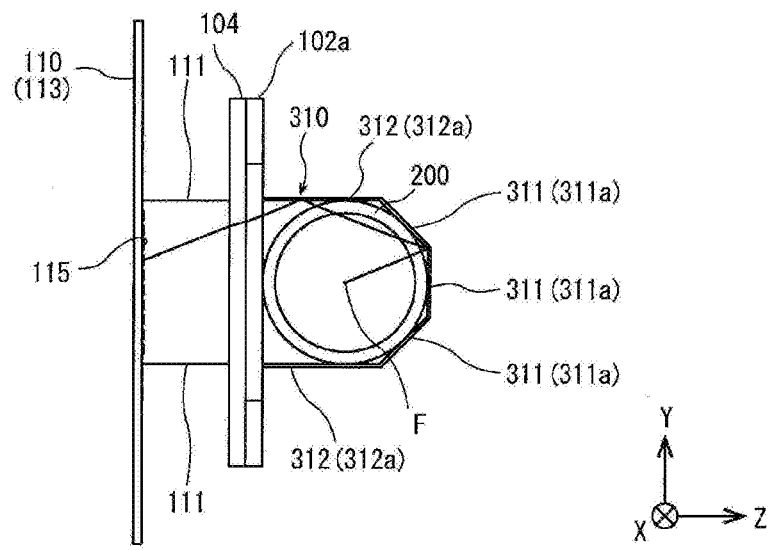

FIG. 5 is a light ray diagram of ultraviolet light emitting from the light source unit 100 of this embodiment, FIG. 5A is a light ray diagram showing an example of a light ray incident on a surface of the outer peripheral surface of the optical fiber F (an area of half of the outer peripheral surface disposed at the upstream side in the Z-axis direction), and FIG. 5B is a light ray diagram showing an example of a light ray incident on the other side of the outer peripheral surface of the optical fiber F (an area of half of the outer peripheral surface disposed at the downstream side in the Z-axis direction).

As shown in FIG. 5A, ultraviolet light emitted from the LED devices 115 of the light source unit 100 is emitted from the window 104 by the guidance of the pair of inner reflecting mirrors 111. Furthermore, ultraviolet light emitted from the window 104 goes into the light transmitting pipe 200 directly or by the guidance of the pair of second reflecting surfaces 312a, and irradiates a surface of the outer peripheral surface of the optical fiber F (an area of half of the outer peripheral surface disposed at the upstream side in the Z-axis direction). Furthermore, as shown in FIG. 5B, a portion of ultraviolet light emitted from the window 104 goes out of the light transmitting pipe 200 by the guidance of the pair of second reflecting surfaces 312a, reflects off the first reflecting surface 311a, then goes into the light transmitting pipe 200, and irradiates the other side of the outer peripheral surface of the optical fiber F (an area of half of the outer peripheral surface disposed at the downstream side in the Z-axis direction). According to the configuration of this embodiment as described above, it is possible to perform ultraviolet light irradiation on the entire outer peripheral surface of the optical fiber F (as described in detail below).

Returning to FIGS. 1 and 2, the mirror frame 320 of the mirror module 300 is a plate-shaped member made of metal that supports the reflecting mirror 310 and radiates heat from the reflecting mirror 310. The mirror frame 320 has a concave part 322 (a receiving part) for receiving the reflecting mirror 310 and the light transmitting pipe 200 on one side surface (a surface on the side facing the light source unit 100), and when the mirror module 300 is attached the front panel 102a of the case 102, the reflecting mirror 310 and the light transmitting pipe 200 are received and fixed in the concave part 322. Furthermore, when the reflecting mirror 310 is received and fixed in the concave part 322, the mirror frame 320 is closely connected and thermally joined to the first reflecting part 311 and the second reflecting part 312 of the reflecting mirror 310. The mirror frame 320 has a plurality of heat radiation fins 324 for efficiently radiating heat from the mirror frame 320 on the other side surface. Thus, heat transferred from the reflecting mirror 310 to the mirror frame 320 is efficiently radiated in air through the heat radiation fins 324.

The cooling fan 330 is an apparatus for cooling the heat radiation fins 324 of the mirror frame 320. Because outside air is blown to the heat radiation fins 324 by the cooling fan 330, the heat radiation fins 324 are cooled more efficiently than natural air cooling.

Figure 6A:
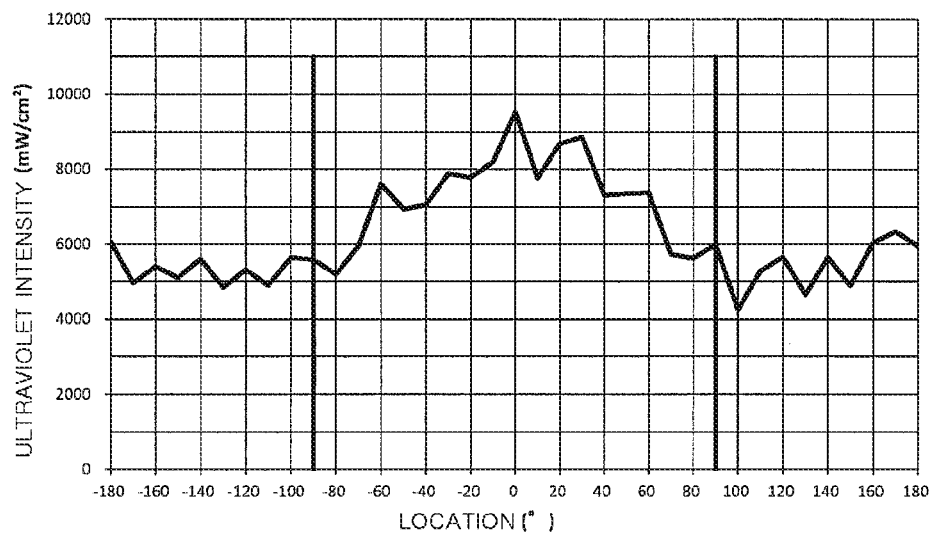
FIG. 6A and FIG. 6B are respectively a diagram showing simulation results of ultraviolet intensity distribution on an outer peripheral surface of an optical fiber F irradiated by the light illuminating apparatus according to the first embodiment.
Figure 6B:
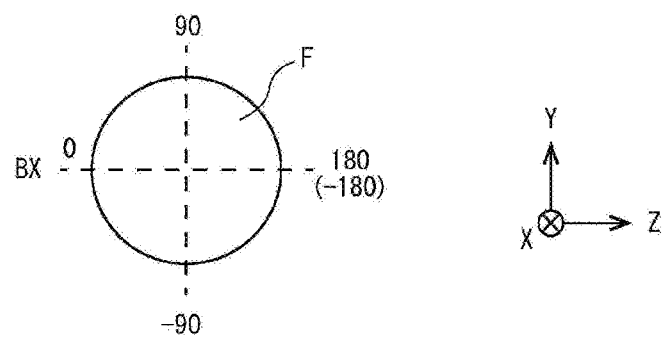

The following is a description of the ultraviolet intensity on the outer peripheral surface of the optical fiber F irradiated by the light illuminating apparatus 1 of this embodiment. FIG. 6 is a diagram showing simulation results of ultraviolet intensity distribution on the outer peripheral surface of the optical fiber F irradiated by the light illuminating apparatus 1 of this embodiment, and FIG. 6A is a graph of ultraviolet intensity distribution at the center of the window 104 in the X-axis direction, and FIG. 6B is a diagram illustrating the horizontal axis of FIG. 6A. As shown in FIG. 6B, the horizontal axis of FIG. 6A is a location of the outer peripheral surface when a location at which the outer peripheral surface of the optical fiber F and the straight line BX (FIG. 4) intersect is set to 0°, and the angle of clockwise rotation is indicated by 0 to 180° (i.e., +) and the angle of counterclockwise rotation is indicated by 0 to −180° (i.e., −). Furthermore, the longitudinal axis of FIG. 6A is ultraviolet intensity (mW/cm$^2$).

As shown in FIG. 6, it can be seen that the ultraviolet intensity irradiating a surface of the outer peripheral surface of the optical fiber F (0° to −90°, 0° to 90°) is somewhat higher than the ultraviolet intensity irradiating the other side of the outer peripheral surface of the optical fiber F (−180° to −90°, −180° to 90°), but a predetermined intensity (for example, 4000 (mW/cm$^2$)) necessary to cure a coating agent coated on the entire outer peripheral surface of the optical fiber F is obtained. Furthermore, in this embodiment, a maximum value of ultraviolet intensity on the outer peripheral surface of the optical fiber F was 9532 (mW/cm$^2$), a minimum value was 4243 (mW/cm$^2$), and minimum value/maximum value was 44.5%.

According to the configuration of this embodiment as described above, it is possible to allow an approximately uniform intensity of ultraviolet light irradiation onto the outer peripheral surface of the optical fiber F. As a result, a coating agent coated on the outer peripheral surface of the optical fiber F is uniformly cured. Furthermore, according to the configuration of this embodiment, a distance (about 10 mm) between the light source unit 100 and the optical fiber F can be set to be significantly short as compared to traditional configuration using an elliptical mirror, thereby realizing the light illuminating apparatus 1 that is small in size as compared to traditional one.

Although this embodiment has been hereinabove described, the present disclosure is not limited to the disclosed embodiment and various variations may be made within the scope of the technical spirit of the present disclosure.

Although this embodiment is described that the light illuminating apparatus 1 is, for example, an apparatus for curing a curing agent coated on the optical fiber F pulled out as a string, the use of the light illuminating apparatus 1 is not limited thereto. For example, the target object may have a shape of a line, a sphere or a particle, and in this case, a coating agent coated on the outer peripheral surface of the target object can be also cured. Furthermore, the target object may be, for example, in liquid phase, and in this case, the target object can be sterilized by shedding ultraviolet light on the target object.

Furthermore, although the optical fiber F moving (traveling) in one direction is described as the target object in this embodiment, the target object is not necessarily moving, and ultraviolet light irradiation may be performed on a stationary object.

(First Variation)

Figure 7:
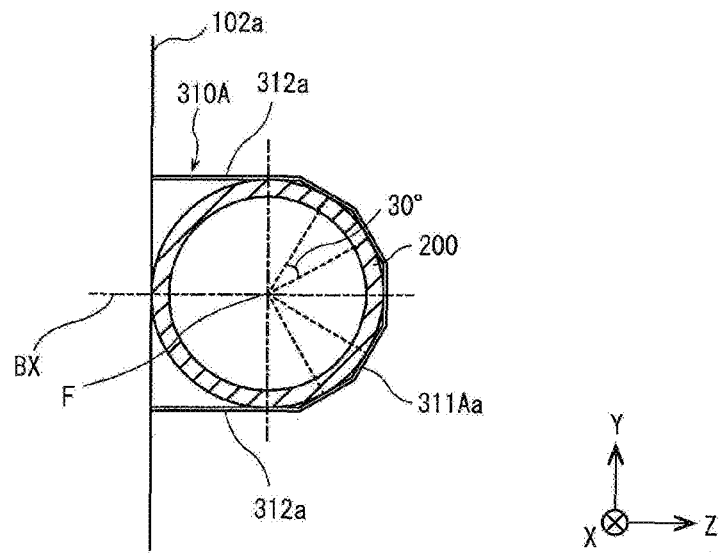
FIG. 7 is a cross-sectional view showing a first variation of the light illuminating apparatus according to the first embodiment of the present disclosure.

FIG. 7 is a cross-sectional view showing a first variation of the first embodiment of the present disclosure. A reflecting mirror 310A of this variation is different from the reflecting mirror 310 according to the first embodiment in the respect that it has five first reflecting surfaces 311Aa, and normal lines passing through the center of each first reflecting surface 311Aa pass through the center axis (i.e., the optical fiber F) of the light transmitting pipe 200, and are installed at an angular interval of 30° around the optical fiber F. That is, each first reflecting surface 311Aa of this variation is equivalent to one side of a regular dodecagon with the optical fiber F serving as an inner center, and is line-symmetric with respect to the straight line BX.

Figure 8A:
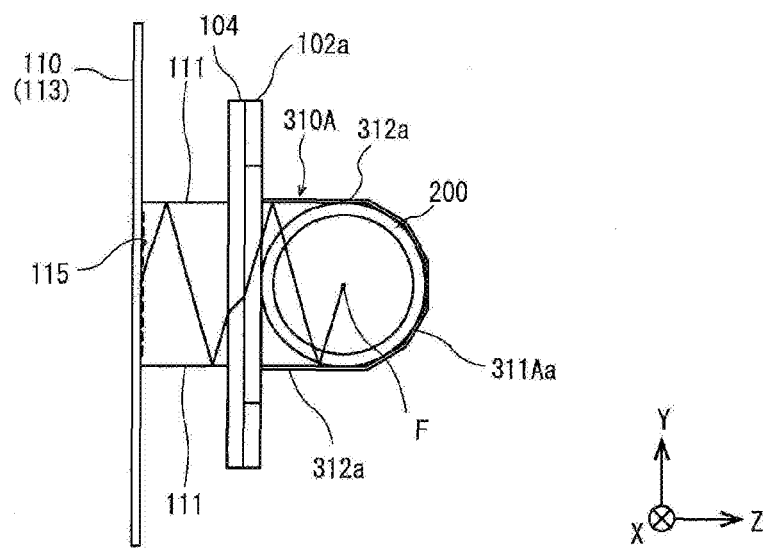
FIG. 8A and FIG. 8B are respectively a light ray diagram of ultraviolet light in the case that the first variation of FIG. 7 is used.
Figure 8B:
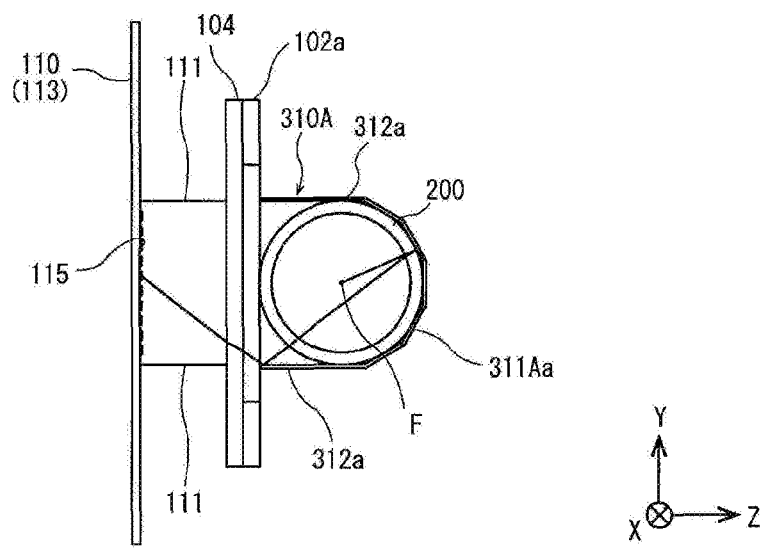
Figure 9:
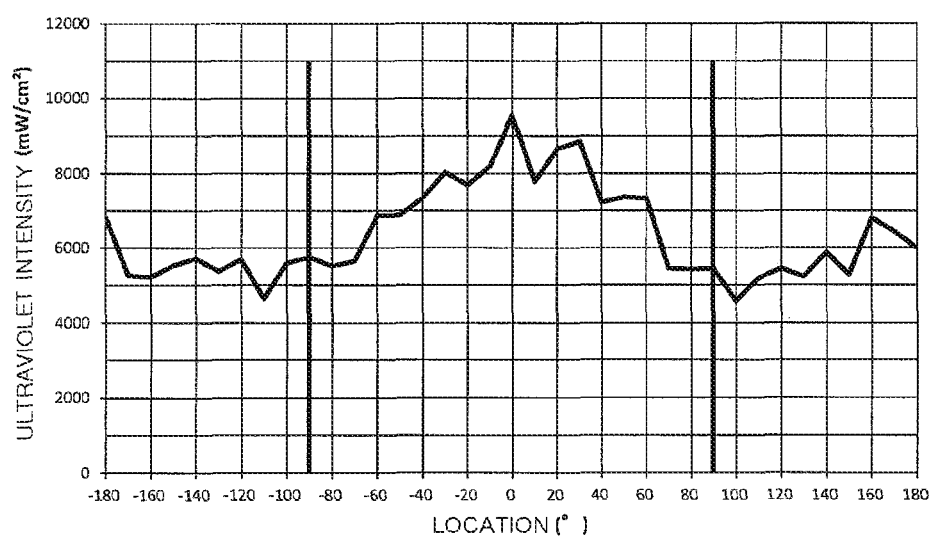
FIG. 9 is a diagram showing simulation results of ultraviolet intensity distribution on an outer peripheral surface of an optical fiber F in the case that the first variation of FIG. 7 is used.

FIG. 8 is a light ray diagram of ultraviolet light in the case that the reflecting mirror 310A of this variation is used, FIG. 8A is a light ray diagram showing an example of a light ray incident on a surface of the outer peripheral surface of the optical fiber F (an area of half of the outer peripheral surface disposed at the upstream side in the Z-axis direction), and FIG. 8B is a light ray diagram showing an example of a light ray incident on the other side of the outer peripheral surface of the optical fiber F (an area of half of the outer peripheral surface disposed at the downstream side in the Z-axis direction). Furthermore, FIG. 9 is a diagram showing simulation results of ultraviolet intensity distribution on the outer peripheral surface of the optical fiber F in the case that the reflecting mirror 310A of this variation is used.

As shown in FIG. 8A, in the case that the reflecting mirror 310A of this variation is used, ultraviolet light emitted from the LED device 115 of the light source unit 100 is emitted from the window 104 by the guidance of the pair of inner reflecting mirrors 111 in the same way as the first embodiment. Furthermore, ultraviolet light emitted from the window 104 goes into the light transmitting pipe 200 directly or by the guidance of the pair of second reflecting surfaces 312a, and irradiates a surface of the outer peripheral surface of the optical fiber F (an area of half of the outer peripheral surface disposed at the upstream side in the Z-axis direction). Furthermore, as shown in FIG. 8B, a portion of ultraviolet light emitted from the window 104 goes out of the light transmitting pipe 200 by the guidance of the pair of second reflecting surfaces 312a, reflects off the first reflecting surface 311Aa, then goes into the light transmitting pipe 200, and irradiates the other side of the outer peripheral surface of the optical fiber F (an area of half of the outer peripheral surface disposed at the downstream side in the Z-axis direction). In the case that the reflecting mirror 310A of this variation is used as described above, it is also possible to perform ultraviolet light irradiation on the entire outer peripheral surface of the optical fiber F. Furthermore, as a result, as shown in FIG. 9, the ultraviolet intensity irradiating a surface of the outer peripheral surface of the optical fiber F (0° to −90°, 0° to 90°) is somewhat higher than the ultraviolet intensity irradiating the other side of the outer peripheral surface of the optical fiber F (−180° to −90°, −180° to 90°), but a predetermined intensity (for example, 4000 (mW/cm$^2$)) necessary to cure a coating agent coated on the entire outer peripheral surface of the optical fiber F is obtained. Furthermore, in this variation, a maximum value of ultraviolet intensity on the outer peripheral surface of the optical fiber F was 9541 (mW/cm$^2$), a minimum value was 4561 (mW/cm$^2$), and minimum value/maximum value was 47.8%.

(Second Variation)

Figure 10:
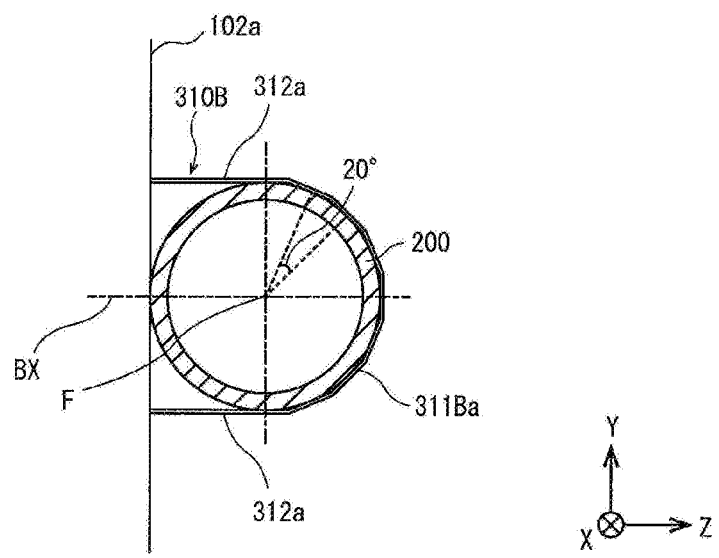
FIG. 10 is a cross-sectional view showing a second variation of a light illuminating apparatus according to the first embodiment of the present disclosure.

FIG. 10 is a cross-sectional view showing a second variation of the first embodiment of the present disclosure. A reflecting mirror 310B of this variation is different from the reflecting mirror 310 according to the first embodiment in the respect that it has seven first reflecting surfaces 311Ba, and normal lines passing through the center of each first reflecting surface 311Ba pass through the center axis (i.e., the optical fiber F) of the light transmitting pipe 200, and are installed at an angular interval of 20° around the optical fiber F. That is, each first reflecting surface 311Ba of this variation is equivalent to one side of a regular octadecagon with the optical fiber F serving as an inner center, and is line-symmetric with respect to the straight line BX.

Figure 11A:
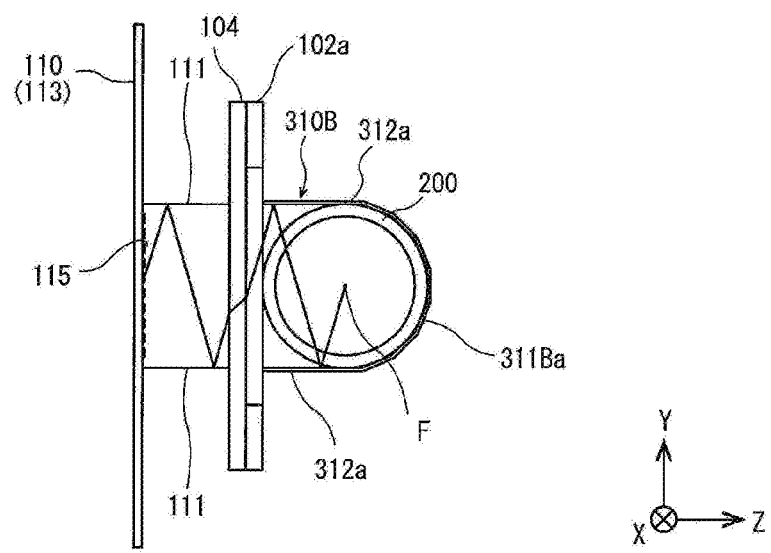
FIG. 11A and FIG. 11B are respectively a light ray diagram of ultraviolet light in the case that the second variation of FIG. 10 is used.
Figure 11B:
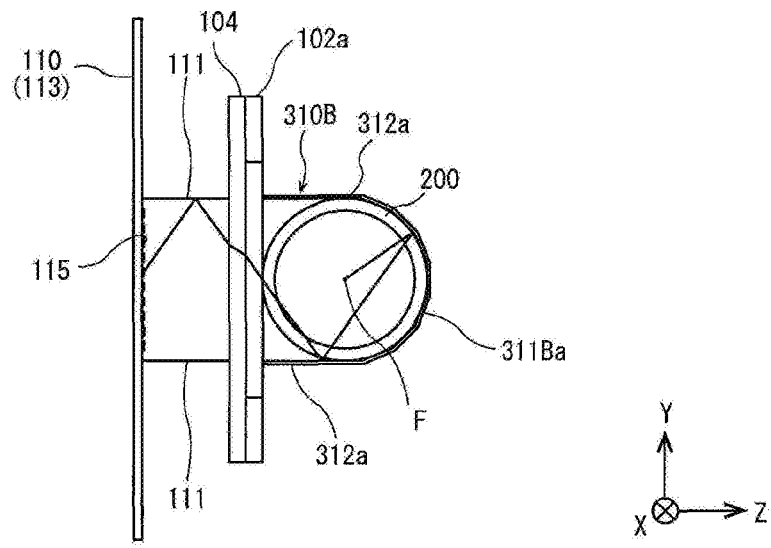
Figure 12:
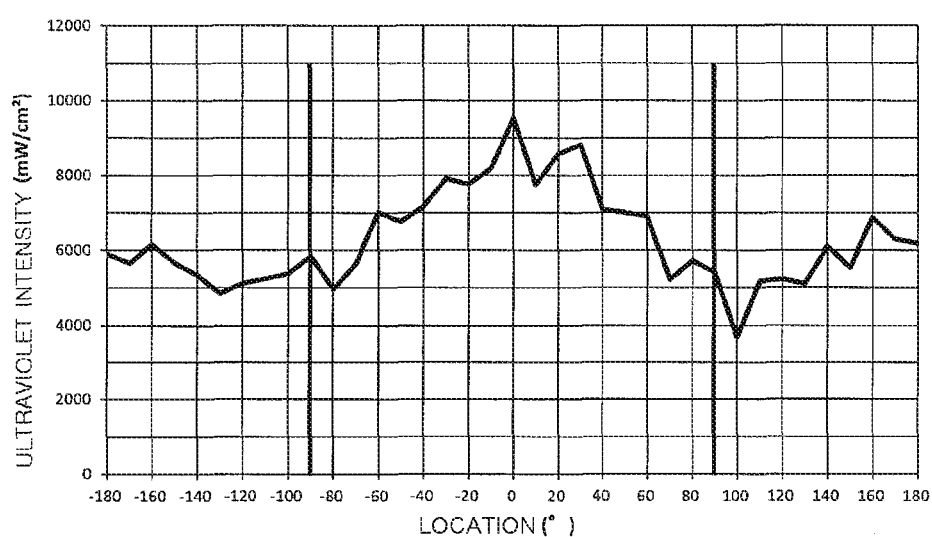
FIG. 12 is a diagram showing simulation results of ultraviolet intensity distribution on an outer peripheral surface of an optical fiber F in the case that the second variation of FIG. 10 is used.

FIG. 11 is a light ray diagram of ultraviolet light in the case that the reflecting mirror 310B of this variation is used, FIG. 11A is a light ray diagram showing an example of a light ray incident on a surface of the outer peripheral surface of the optical fiber F (an area of half of the outer peripheral surface disposed at the upstream side in the Z-axis direction), and FIG. 11B is a light ray diagram showing an example of a light ray incident on the other side of the outer peripheral surface of the optical fiber F (an area of half of the outer peripheral surface disposed at the downstream side in the Z-axis direction). Furthermore, FIG. 12 is a diagram showing simulation results of ultraviolet intensity distribution on the outer peripheral surface of the optical fiber F in the case that the reflecting mirror 310B of this variation is used.

As shown in FIGS. 11A and 11B, in the case that the reflecting mirror 310B of this variation is used, it is also possible to perform ultraviolet light irradiation on the entire outer peripheral surface of the optical fiber F in the same way as the first embodiment. Furthermore, as a result, as shown in FIG. 12, the ultraviolet intensity irradiating a surface of the outer peripheral surface of the optical fiber F (0° to −90°, 0° to 90°) is somewhat higher than the ultraviolet intensity irradiating the other side of the outer peripheral surface of the optical fiber F (−180° to −90°, −180° to 90°), but a predetermined intensity (for example, 3500 (mW/cm$^2$)) necessary to cure a coating agent coated on the entire outer peripheral surface of the optical fiber F is obtained. Furthermore, in this variation, a maximum value of ultraviolet intensity on the outer peripheral surface of the optical fiber F was 9531 (mW/cm$^2$), a minimum value was 3681 (mW/cm$^2$), and minimum value/maximum value was 38.6%.

(Third Variation)

Figure 13:
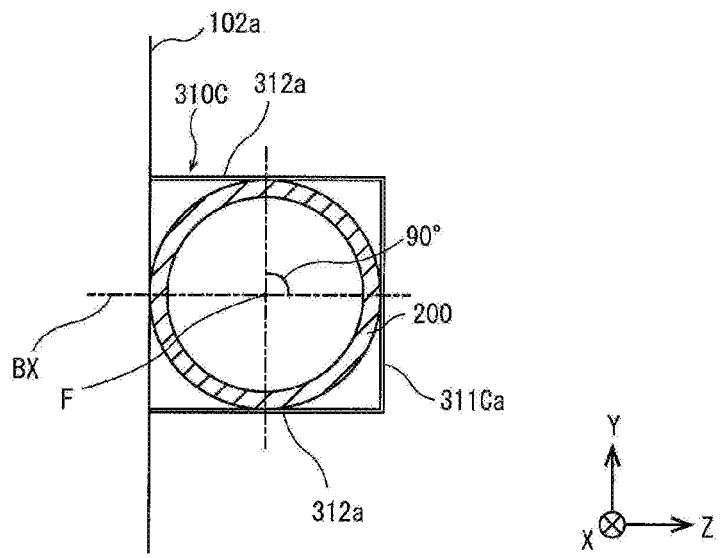
FIG. 13 is a cross-sectional view showing a third variation of the light illuminating apparatus according to the first embodiment of the present disclosure.

FIG. 13 is a cross-sectional view showing a third variation of the first embodiment of the present disclosure. A reflecting mirror 310C of this variation is different from the reflecting mirror 310 according to the first embodiment in the respect that it has one first reflecting surface 311Ca, and a normal line passing through the center of the first reflecting surface 311Ca passes through the center axis (i.e., the optical fiber F) of the light transmitting pipe 200, and is installed to overlap with the straight line BX. That is, the first reflecting surface 311Ca of this variation is equivalent to one side of a square with the optical fiber F serving as an inner center, and is line-symmetric with respect to the straight line BX.

Figure 14A:
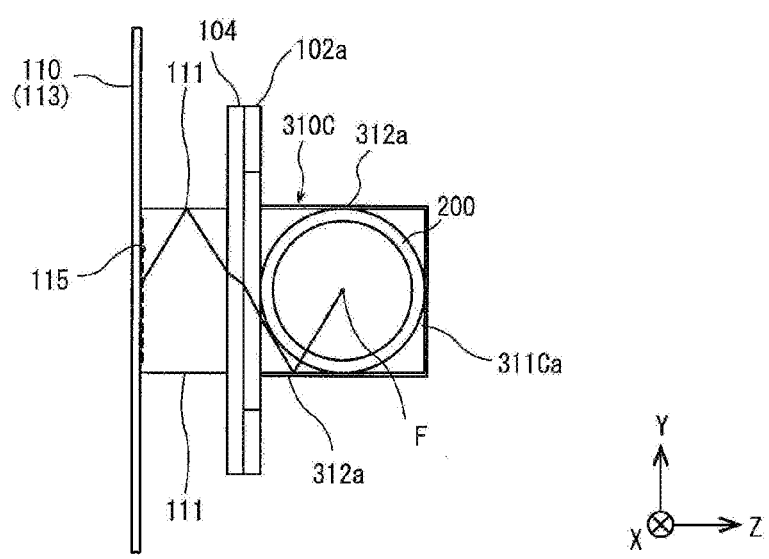
FIG. 14A and FIG. 14B are respectively a light ray diagram of ultraviolet light in the case that the third variation of FIG. 13 is used.
Figure 14B:
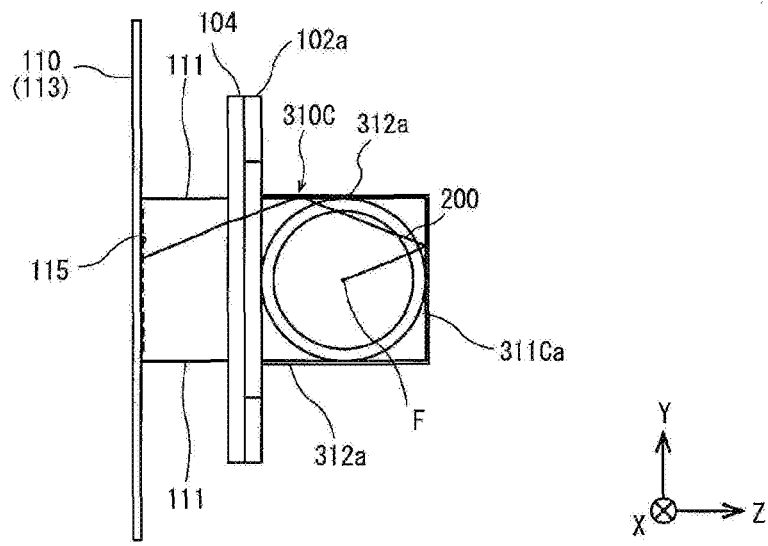
Figure 15:
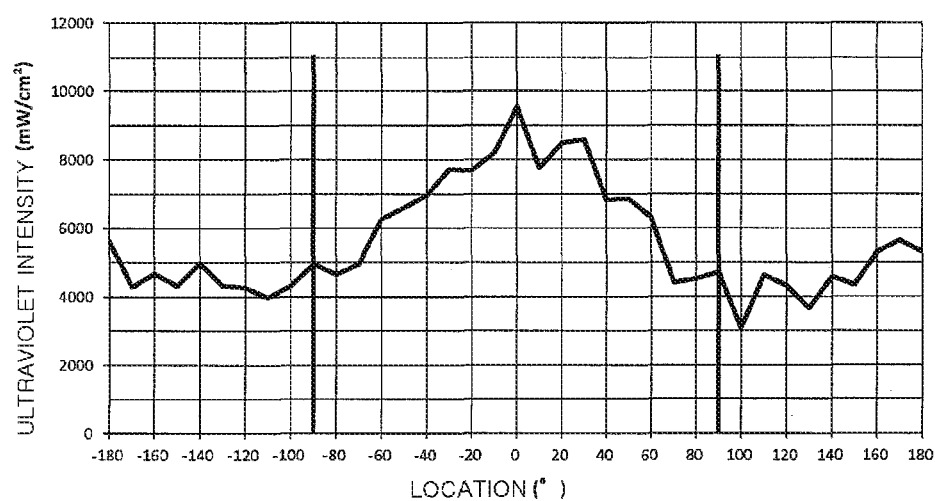
FIG. 15 is a diagram showing simulation results of ultraviolet intensity distribution on an outer peripheral surface of an optical fiber F in the case that the third variation of FIG. 13 is used.

FIG. 14 is a light ray diagram of ultraviolet light in the case that the reflecting mirror 310C of this variation is used, FIG. 14A is a light ray diagram showing an example of a light ray incident on a surface of the outer peripheral surface of the optical fiber F (an area of half of the outer peripheral surface disposed at the upstream side in the Z-axis direction), and FIG. 14B is a light ray diagram showing an example of a light ray incident on the other side of the outer peripheral surface of the optical fiber F (an area of half of the outer peripheral surface disposed at the downstream side in the Z-axis direction). Furthermore, FIG. 15 is a diagram showing simulation results of ultraviolet intensity distribution on the outer peripheral surface of the optical fiber F in the case that the reflecting mirror 310C of this variation is used.

As shown in FIGS. 14A and 14B, in the case that the reflecting mirror 310C of this variation is used, it is also possible to perform ultraviolet light irradiation on the entire outer peripheral surface of the optical fiber F in the same way as the first embodiment. Furthermore, as a result, as shown in FIG. 15, the ultraviolet intensity irradiating a surface of the outer peripheral surface of the optical fiber F (0° to −90°, 0° to 90°) is somewhat higher than the ultraviolet intensity irradiating the other side of the outer peripheral surface of the optical fiber F (−180° to −90°, −180° to 90°), but a predetermined intensity (for example, 3000 (mW/cm$^2$)) necessary to cure a coating agent coated on the entire outer peripheral surface of the optical fiber F is obtained. Furthermore, in this variation, a maximum value of ultraviolet intensity on the outer peripheral surface of the optical fiber F was 9537 (mW/cm$^2$), a minimum value was 3070 (mW/cm$^2$), and minimum value/maximum value was 32.1%.

(Fourth Variation)

Figure 16:
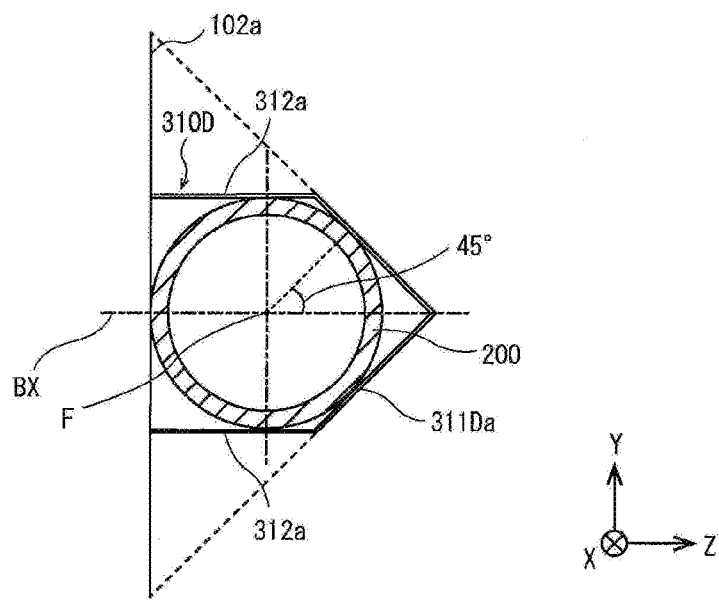
FIG. 16 is a cross-sectional view showing a fourth variation of the light illuminating apparatus according to the first embodiment of the present disclosure.

FIG. 16 is a cross-sectional view showing a fourth variation of the first embodiment of the present disclosure. A reflecting mirror 310D of this variation is different from the reflecting mirror 310 according to the first embodiment in the respect that it has two first reflecting surfaces 311Da. In this variation, the two first reflecting surfaces 311Da are equivalent to parts of oblique sides (dotted lines in FIG. 16) of an isosceles right triangle with the optical fiber F serving as an inner center, and are line-symmetric with respect to the straight line BX. Furthermore, normal lines of the first reflecting surfaces 311Da passing through the center axis (i.e., the optical fiber F) of the light transmitting pipe 200 are inclined at an angle of 45° to the straight line BX.

Figure 17A:
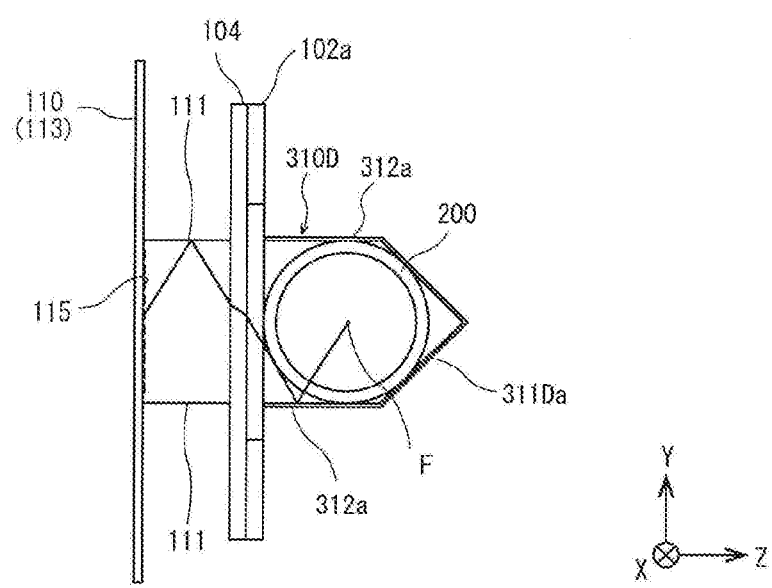
FIG. 17A and FIG. 17B are respectively a light ray diagram of ultraviolet light in the case that the fourth variation of FIG. 16 is used.
Figure 17B:
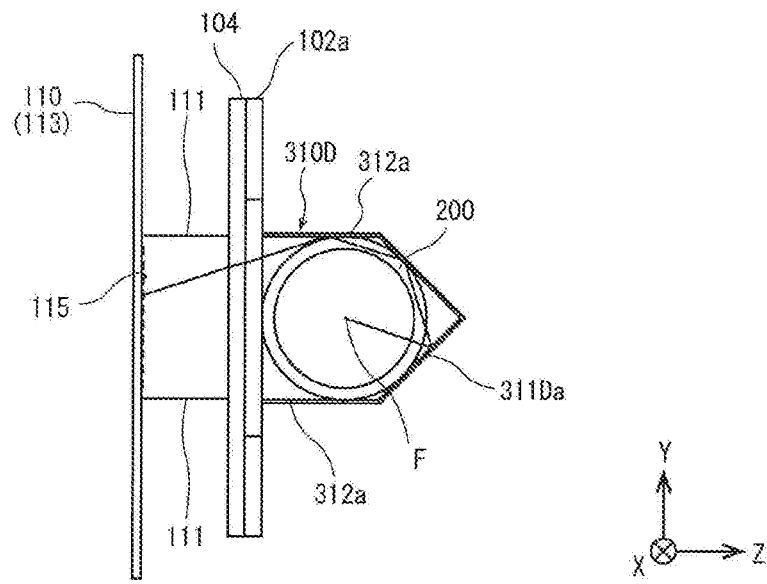
Figure 18:
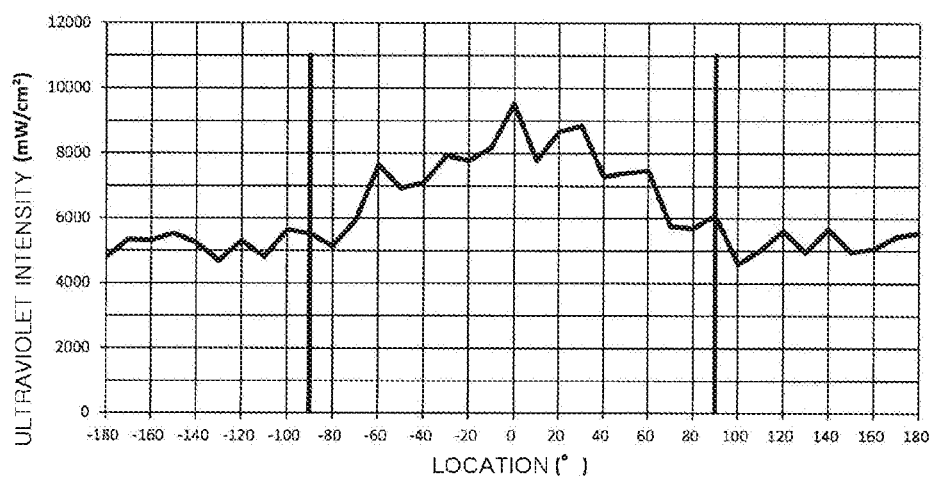
FIG. 18 is a diagram showing simulation results of ultraviolet intensity distribution on an outer peripheral surface of an optical fiber F in the case that the fourth variation of FIG. 16 is used.

FIG. 17 is a light ray diagram of ultraviolet light in the case that the reflecting mirror 310D of this variation is used, FIG. 17A is a light ray diagram showing an example of a light ray incident on a surface of the outer peripheral surface of the optical fiber F (an area of half of the outer peripheral surface disposed at the upstream side in the Z-axis direction), and FIG. 17B is a light ray diagram showing an example of a light ray incident on the other side of the outer peripheral surface of the optical fiber F (an area of half of the outer peripheral surface disposed at the downstream side in the Z-axis direction). Furthermore, FIG. 18 is a diagram showing simulation results of ultraviolet intensity distribution on the outer peripheral surface of the optical fiber F in the case that the reflecting mirror 310D of this variation is used.

As shown in FIGS. 17A and 17B, in the case that the reflecting mirror 310D of this variation is used, it is also possible to perform ultraviolet light irradiation on the entire outer peripheral surface of the optical fiber F in the same way as the first embodiment. Furthermore, as a result, as shown in FIG. 18, the ultraviolet intensity irradiating a surface of the outer peripheral surface of the optical fiber F (0° to −90°, 0° to 90°) is somewhat higher than the ultraviolet intensity irradiating the other side of the outer peripheral surface of the optical fiber F (−180° to −90°, −180° to 90°), but a predetermined intensity (for example, 4000 (mW/cm$^2$)) necessary to cure a coating agent coated on the entire outer peripheral surface of the optical fiber F is obtained. Furthermore, in this variation, a maximum value of ultraviolet intensity on the outer peripheral surface of the optical fiber F was 9537 (mW/cm$^2$), a minimum value was 4577 (mW/cm$^2$), and minimum value/maximum value was 48.0%.

(Fifth Variation)

Figure 19:
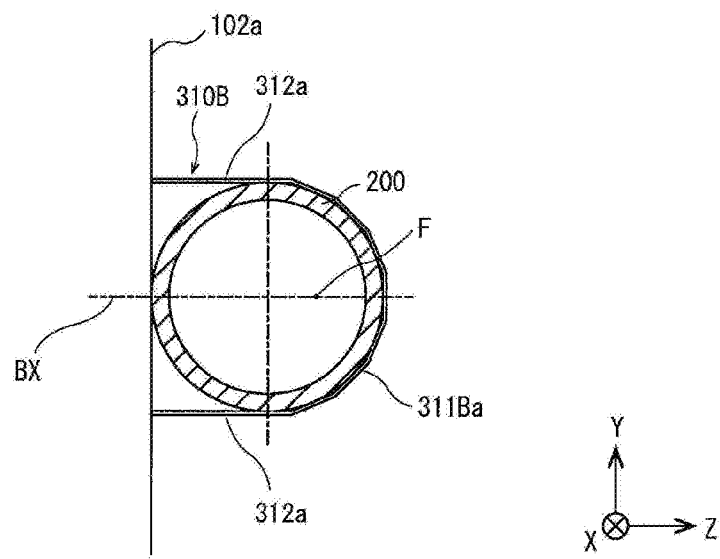
FIG. 19 is a cross-sectional view showing a fifth variation of the light illuminating apparatus according to the first embodiment of the present disclosure.

FIG. 19 is a cross-sectional view showing a fifth variation of the first embodiment of the present disclosure. This variation has the reflecting mirror 310B according to the second variation, and is different from the second variation in the respect that the optical fiber F is placed with an offset of about 5 mm in the Z-axis direction relative to the center axis of the light transmitting pipe 200.

Figure 20A:
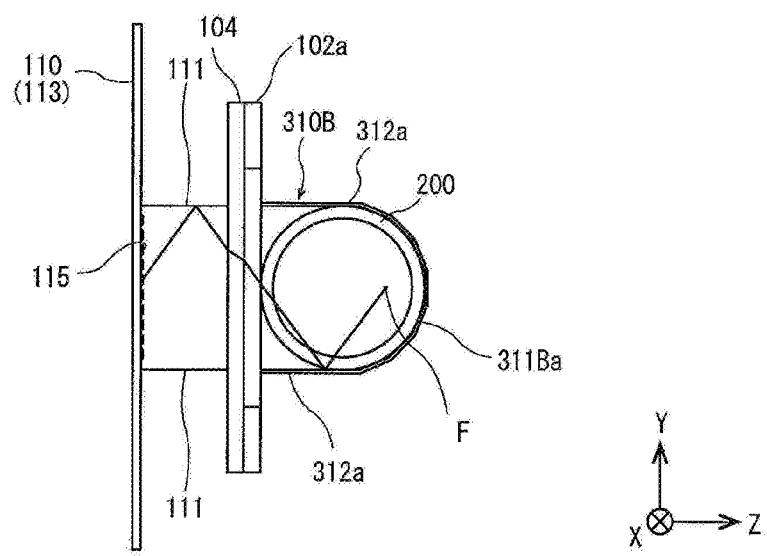
FIG. 20A and FIG. 20B are respectively a light ray diagram of ultraviolet light in the case that the fifth variation of FIG. 19 is used.
Figure 20B:
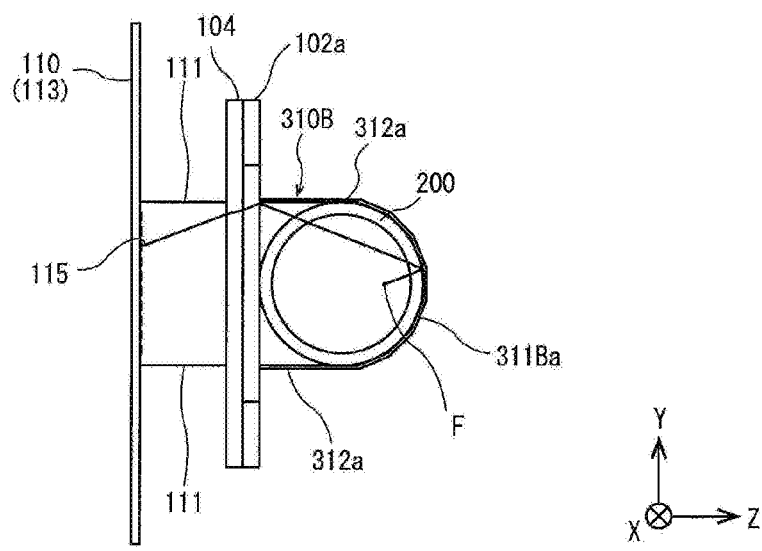

FIG. 20 is a light ray diagram of ultraviolet light of this variation, FIG. 20A is a light ray diagram showing an example of a light ray incident on a surface of the outer peripheral surface of the optical fiber F (an area of half of the outer peripheral surface disposed at the upstream side in the Z-axis direction), and FIG. 20B is a light ray diagram showing an example of a light ray incident on the other side of the outer peripheral surface of the optical fiber F (an area of half of the outer peripheral surface disposed at the downstream side in the Z-axis direction). Furthermore, FIG. 21 is a diagram showing simulation results of ultraviolet intensity distribution on the outer peripheral surface of the optical fiber F of this variation.

Figure 21:
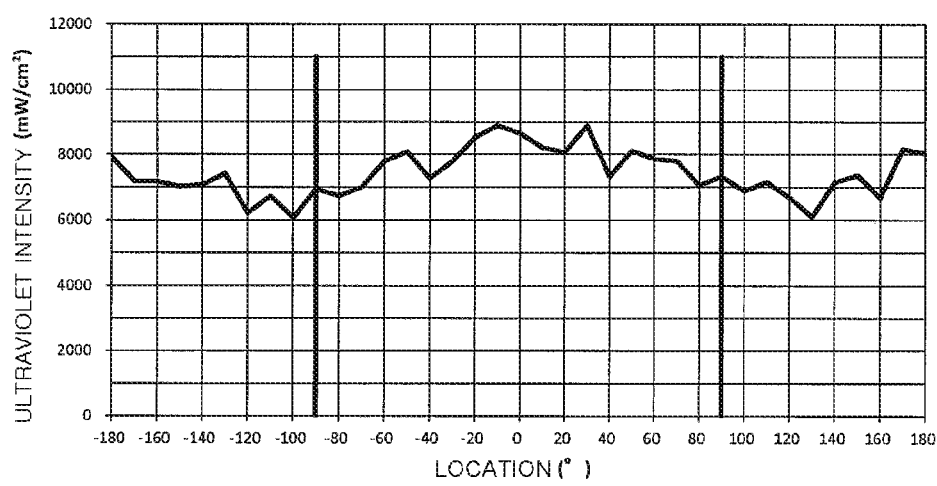
FIG. 21 is a diagram showing simulation results of ultraviolet intensity distribution on an outer peripheral surface of an optical fiber F in the case that the fifth variation of FIG. 19 is used.

As shown in FIGS. 20A and 20B, in this variation, it is also possible to perform ultraviolet light on the entire outer peripheral surface of the optical fiber F in the same way as the second variation, and as shown in FIG. 21, ultraviolet intensity distribution is more flat than the second variation (FIG. 12), and a predetermined intensity (for example, 6000 (mW/cm$^2$)) necessary to cure a coating agent coated on the entire outer peripheral surface of the optical fiber F is obtained. Furthermore, in this variation, a maximum value of ultraviolet intensity on the outer peripheral surface of the optical fiber F was 8889 (mW/cm$^2$), a minimum value was 6052 (mW/cm$^2$), and minimum value/maximum value was 68.1%. Furthermore, although the optical fiber F is placed with an offset of about 5 mm in the Z-axis direction relative to the center axis of the light transmitting pipe 200 in this variation, the present disclosure is not necessarily limited thereto. If ultraviolet light emitted from the LED device 115 of the light source unit 100 enters a space surrounded by the first reflecting surface 311Ba and the second reflecting surface 312a, ultraviolet light repeatedly reflects off the first reflecting surface 311Ba and the second reflecting surface 312a, so ultraviolet light facing various directions exists in the space surrounded by the first reflecting surface 311Ba and the second reflecting surface 312a. Accordingly, even if the optical fiber F is placed with an offset in the Y-axis direction, the direction opposite to the Y-axis direction, or the direction opposite to the Z-axis direction relative to the center axis of the light transmitting pipe 200 (that is, as long as the optical fiber F is placed in the space surrounded by the first reflecting surface 311Ba and the second reflecting surface 312a), ultraviolet intensity distribution on the outer peripheral surface of the optical fiber F is approximately identical to that of this variation, and for example, even in the case that the optical fiber F travels at a location off the center axis of the light transmitting pipe 200, ultraviolet light of sufficient intensity to cure an applied coating agent irradiates the outer peripheral surface of the optical fiber F.

Although the first to third variations and fifth variation have been configured such that the first reflecting surfaces 311Aa, 311Ba, 311Ca are planes, and the respective first reflecting surfaces 311Aa, 311Ba, 311Ca are equivalent to one side of a regular dodecagon, a regular octadecagon, and a square with the optical fiber F serving as an inner center as described above, each first reflecting surface is not necessarily equivalent to one side of a regular polygon as shown in the fourth variation, and any that is equivalent to one side of a polygon ranging from a rectangle to an octadecagon can be used. Furthermore, normal lines passing through the centers of all the first reflecting surfaces do not need to face the center axis of the light transmitting pipe 200.

Furthermore, although the first embodiment and the first to fifth variations describe that all the first reflecting surfaces face the center axis of the light transmitting pipe 200, the present disclosure is not limited thereto, and may be configured such that at least one of the first reflecting surfaces faces the center axis of the light transmitting pipe 200, and in the case of a plurality of first reflecting surfaces, they do not need to be successively arranged.

(Sixth Variation)

Figure 22:
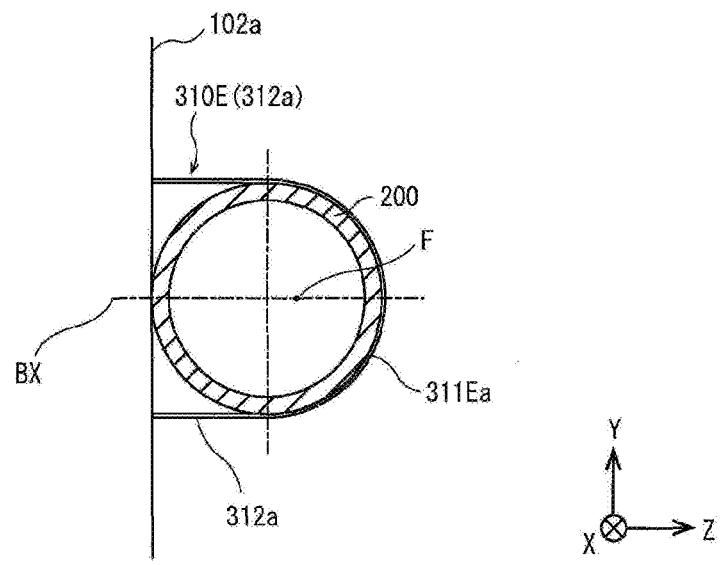
FIG. 22 is a cross-sectional view showing a sixth variation of the light illuminating apparatus according to the first embodiment of the present disclosure.
Figure 23:
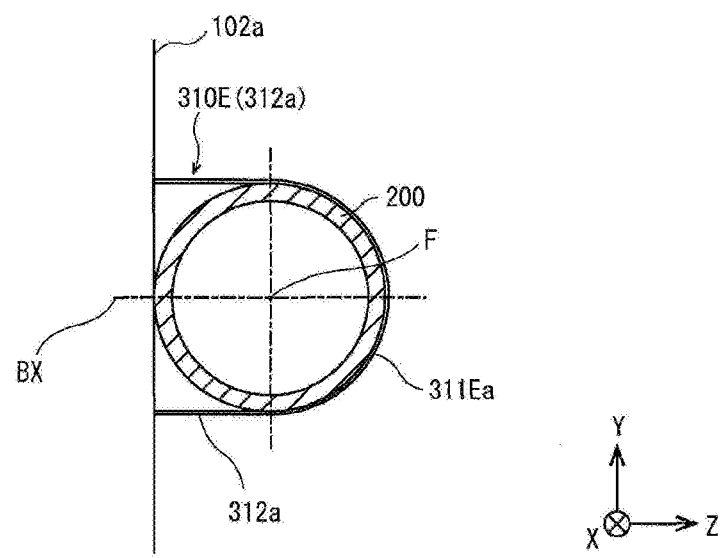
FIG. 23 is a cross-sectional view showing a comparative example of the sixth variation.

FIG. 22 is a cross-sectional view showing a sixth variation of the first embodiment of the present disclosure. Furthermore, FIG. 23 is a cross-sectional view showing a comparative example of the sixth variation. As shown in FIG. 22, a reflecting mirror 310E of this variation is different from that of the first embodiment in the respect that it has a first reflecting surface 311Ea of a semicircular shape, and the optical fiber F is placed with an offset of about 2.5 mm in the Z-axis direction relative to the center axis of the light transmitting pipe 200. Furthermore, as shown in FIG. 23, the comparative example of this variation is different from the configuration of this variation in the respect that the location of the optical fiber F lies on the center axis of the light transmitting pipe 200.

Figure 24A:
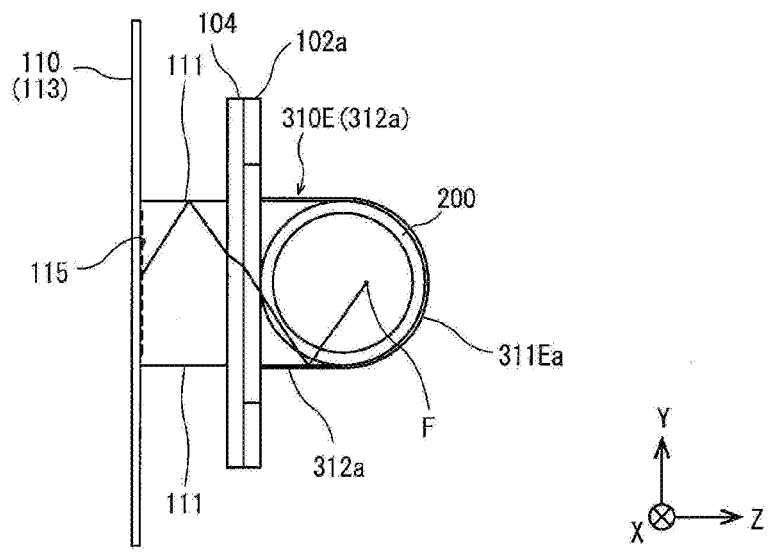
FIG. 24A and FIG. 24B are respectively a light ray diagram of ultraviolet light in the case that the sixth variation is used.
Figure 24B:
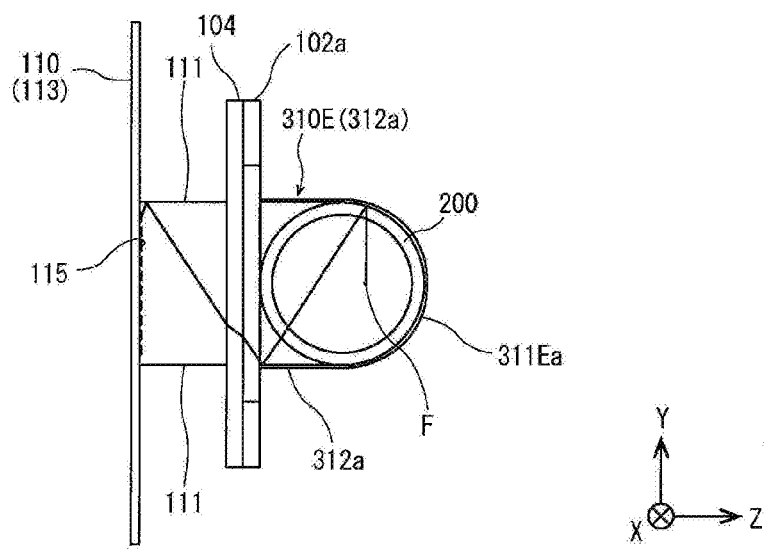
Figure 25A:
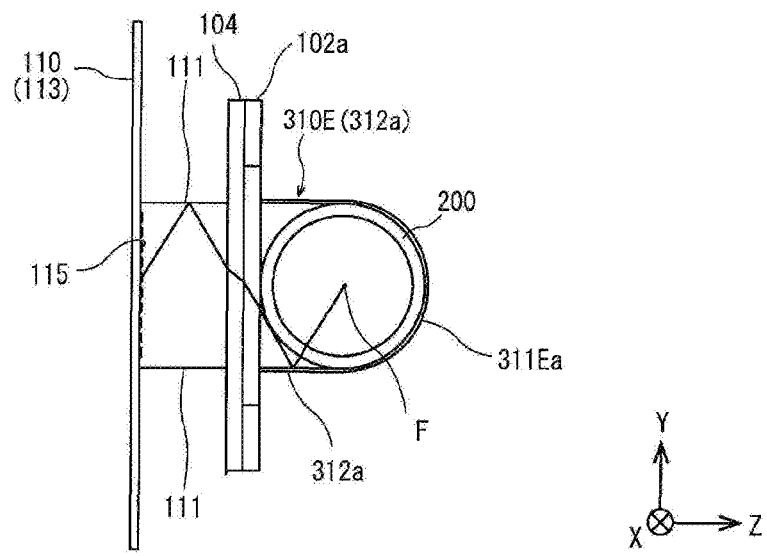
FIG. 25A and FIG. 25B are respectively a light ray diagram of ultraviolet light in the case that the comparative example of the sixth variation is used.
Figure 25B:
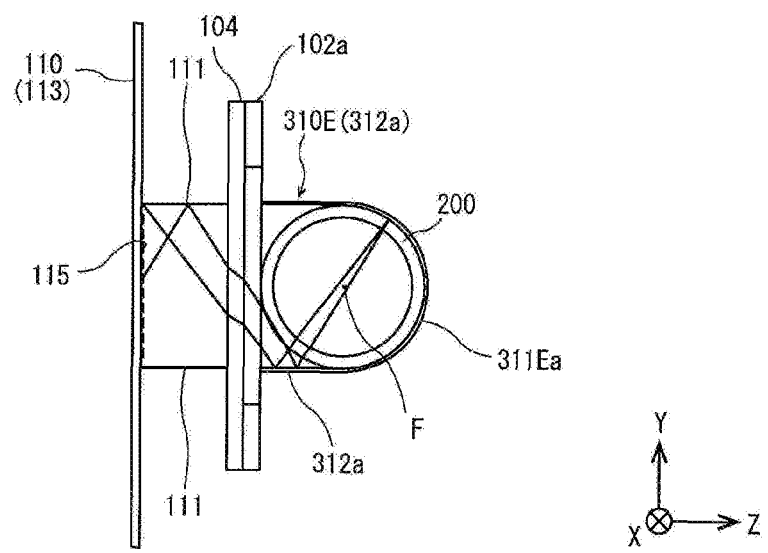

FIG. 24 is a light ray diagram of ultraviolet light in the case that the reflecting mirror 310E of this variation is used, FIG. 24A is a light ray diagram showing an example of a light ray incident on a surface of the outer peripheral surface of the optical fiber F (an area of half of the outer peripheral surface disposed at the upstream side in the Z-axis direction), and FIG. 24B is a light ray diagram showing an example of a light ray incident on the other side of the outer peripheral surface of the optical fiber F (an area of half of the outer peripheral surface disposed at the downstream side in the Z-axis direction). Furthermore, FIG. 25 is a light ray diagram of ultraviolet light of the comparative example of this variation, FIG. 25A is a light ray diagram showing an example of a light ray incident on a surface of the outer peripheral surface of the optical fiber F (an area of half of the outer peripheral surface disposed at the upstream side in the Z-axis direction), and FIG. 25B is a light ray diagram showing an example of a light ray incident on the other side of the outer peripheral surface of the optical fiber F (an area of half of the outer peripheral surface disposed at the downstream side in the Z-axis direction). Furthermore, FIG. 26 is a diagram showing simulation results of ultraviolet intensity distribution on the outer peripheral surface of the optical fiber F of this variation and the comparative example of this variation.

As shown in FIG. 24A, in this variation, ultraviolet light emitted from the LED device 115 of the light source unit 100 is emitted from the window 104 by the guidance of the pair of inner reflecting mirrors 111 in the same way as the first embodiment. Furthermore, ultraviolet light emitted from the window 104 goes into the light transmitting pipe 200 directly or by the guidance of the pair of second reflecting surfaces 312a, and irradiates a surface of the outer peripheral surface of the optical fiber F (an area of half of the outer peripheral surface disposed at the upstream side in the Z-axis direction). Furthermore, as shown in FIG. 24B, a portion of ultraviolet light emitted from the window 104 goes out of the light transmitting pipe 200 by the guidance of the pair of second reflecting surfaces 312a, reflects off the first reflecting surface 311Ea, then goes into the light transmitting pipe 200, and irradiates the other side of the outer peripheral surface of the optical fiber F (an area of half of the outer peripheral surface disposed at the downstream side in the Z-axis direction). In the case that the reflecting mirror 310E of this variation is used as descried above, it is also possible to perform ultraviolet light irradiation on the entire outer peripheral surface of the optical fiber F.

On the other hand, in the comparative example of this variation, as shown in FIG. 25A, ultraviolet light emitted from the window 104 goes into the light transmitting pipe 200 directly or by the guidance of the pair of second reflecting surfaces 312a, and irradiates a surface of the outer peripheral surface of the optical fiber F (an area of half of the outer peripheral surface disposed at the upstream side in the Z-axis direction), while as shown in FIG. 25B, an amount of light rays directly incident on the other side of the outer peripheral surface of the optical fiber F (an area of half of the outer peripheral surface disposed at the downstream side in the Z-axis direction) is small, making it impossible to sufficiently irradiate the other side of the outer peripheral surface of the optical fiber F.

Figure 26:
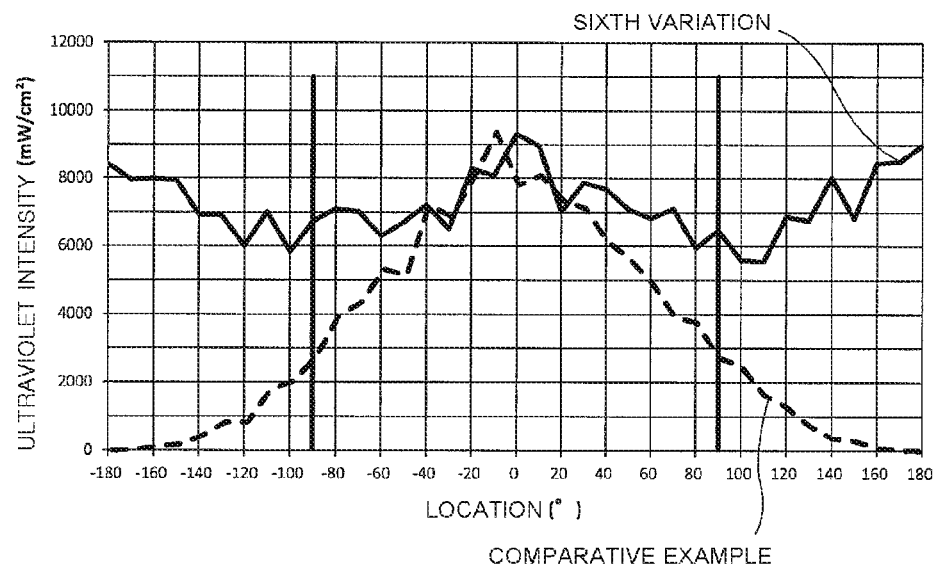
FIG. 26 is a diagram showing simulation results of ultraviolet intensity distribution on an outer peripheral surface of an optical fiber F in the case that the sixth variation and the comparative example of the sixth variation are used.

As a result, as shown in FIG. 26, in this variation, a predetermined intensity (for example, 5000 (mW/cm$^2$)) necessary to cure a coating agent coated on the entire outer peripheral surface of the optical fiber F is obtained, while in the comparative example of this variation, distribution is discrete (namely, the intensity of ultraviolet light on the outer peripheral surface of the optical fiber F varies greatly), making it impossible to obtain a predetermined intensity necessary to cure a coating agent coated on the outer peripheral surface of the optical fiber F. Furthermore, in this variation, a maximum value of ultraviolet intensity on the outer peripheral surface of the optical fiber F was 9305 (mW/cm$^2$), a minimum value was 5541 (mW/cm$^2$), and minimum value/maximum value was 59.5%.

As described above, a semicircular shape having the center disposed on the straight line BX may be applied to the first reflecting surface of the reflecting mirror, and in this case, by changing the location of the optical fiber F, the optical fiber F may be placed in a space between the center of the semicircle and the first reflecting surface.

(Seventh Variation)

Figure 27:
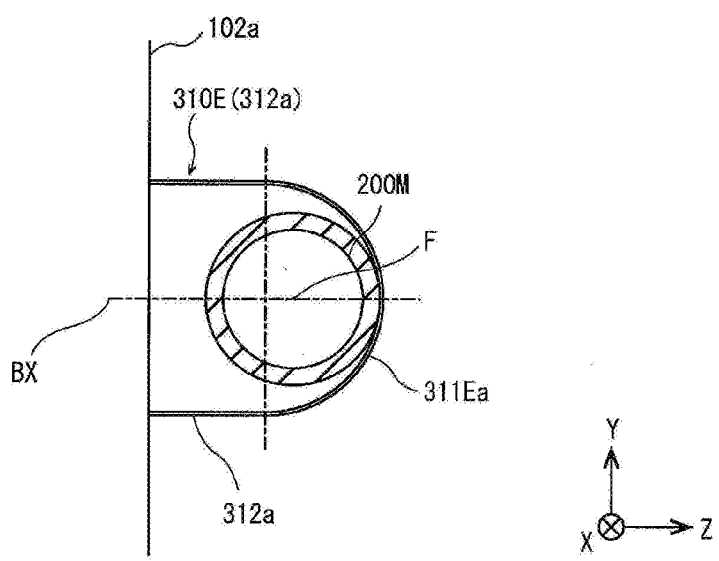
FIG. 27 is a cross-sectional view showing a seventh variation of the light illuminating apparatus according to the first embodiment of the present disclosure.

FIG. 27 is a cross-sectional view showing a seventh variation of the first embodiment of the present disclosure. This variation is different from the sixth variation in the respect that it has a light transmitting pipe 200M with a smaller outer diameter than the light transmitting pipe 200, and the optical fiber F is placed and installed at the center of the light transmitting pipe 200M. In the case that the optical fiber F is placed with an offset in the Z-axis direction relative to the center of the first reflecting surface 311Ea of a semicircular shape as described above, the light transmitting pipe 200M with a small diameter can be used.

Figure 28A:
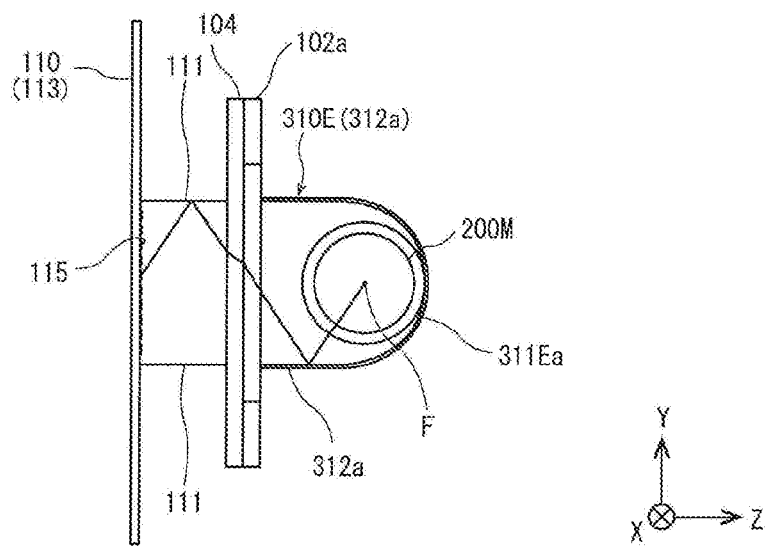
FIG. 28A and FIG. 28B are respectively a light ray diagram of ultraviolet light in the case that the seventh variation of FIG. 27 is used.
Figure 28B:
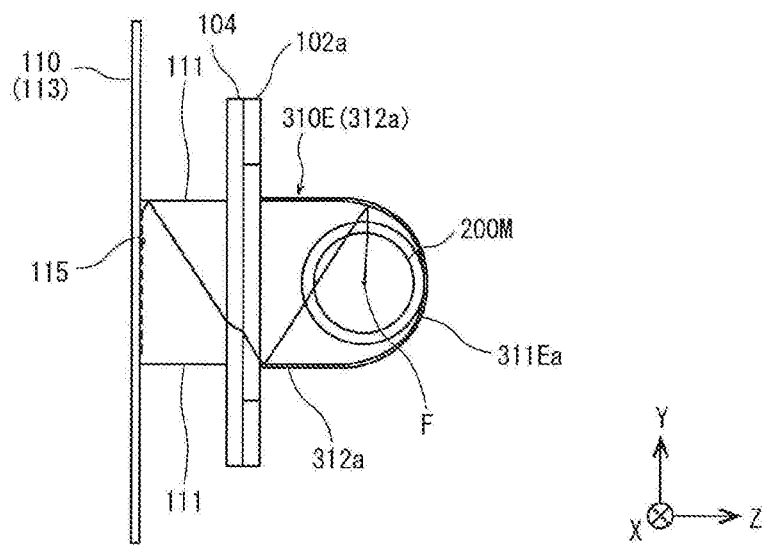
Figure 29:
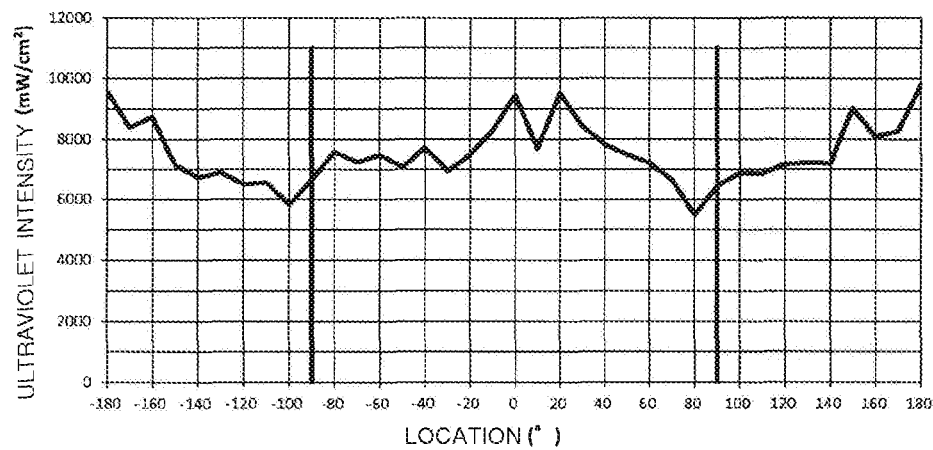
FIG. 29 is a diagram showing simulation results of ultraviolet intensity distribution on an outer peripheral surface of an optical fiber F in the case that the seventh variation of FIG. 27 is used.

FIG. 28 is a light ray diagram of ultraviolet light of this variation, FIG. 28A is a light ray diagram showing an example of a light ray incident on a surface of the outer peripheral surface of the optical fiber F (an area of half of the outer peripheral surface disposed at the upstream side in the Z-axis direction), and FIG. 28B is a light ray diagram showing an example of a light ray incident on the other side of the outer peripheral surface of the optical fiber F (an area of half of the outer peripheral surface disposed at the downstream side in the Z-axis direction). Furthermore, FIG. 29 is a diagram showing simulation results of ultraviolet intensity distribution on the outer peripheral surface of the optical fiber F of this variation.

As shown in FIGS. 28A and 28B, in this variation, it is also possible to perform ultraviolet light irradiation on the entire outer peripheral surface of the optical fiber F in the same way as the sixth variation. Furthermore, as a result, as shown in FIG. 29, ranging from a surface of the outer peripheral surface of the optical fiber F (0° to −90°, 0° to 90°) to the other side (−180° to −90°, −180° to 90°), a predetermined intensity (for example, 5000 (mW/cm$^2$)) necessary to cure a coating agent coated on the outer peripheral surface of the optical fiber F is obtained. Furthermore, in this variation, a maximum value of ultraviolet intensity on the outer peripheral surface of the optical fiber F was 9767 (mW/cm$^2$), a minimum value was 5473 (mW/cm$^2$), and minimum value/maximum value was 56.0%.

(Eighth Variation)

Figure 30:
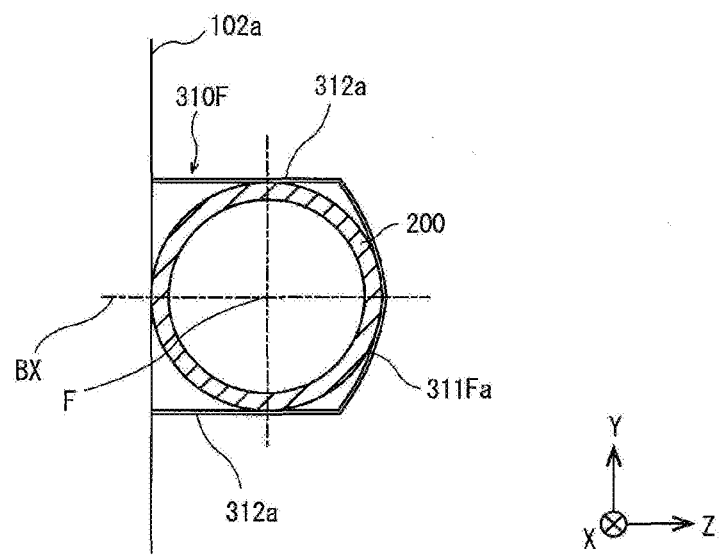
FIG. 30 is a cross-sectional view showing an eighth variation of the light illuminating apparatus according to the first embodiment of the present disclosure.

FIG. 30 is a cross-sectional view showing an eighth variation of the first embodiment of the present disclosure. A reflecting mirror 310F of this variation has a change from the semicircular shape of the first reflecting surface 311Ea of the sixth variation to a paraboloidal shape (a first reflecting surface 311Fa).

Figure 31A:
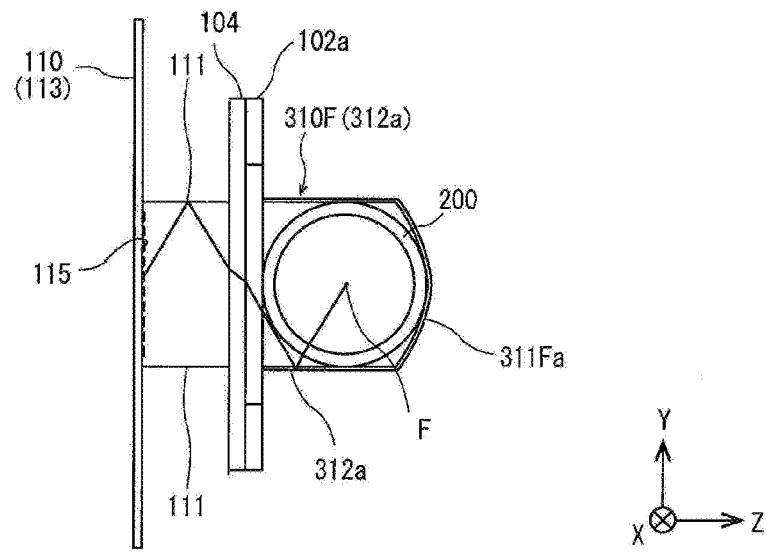
FIG. 31A and FIG. 31B are respectively a light ray diagram of ultraviolet light in the case that the eighth variation of FIG. 30 is used.
Figure 31B:
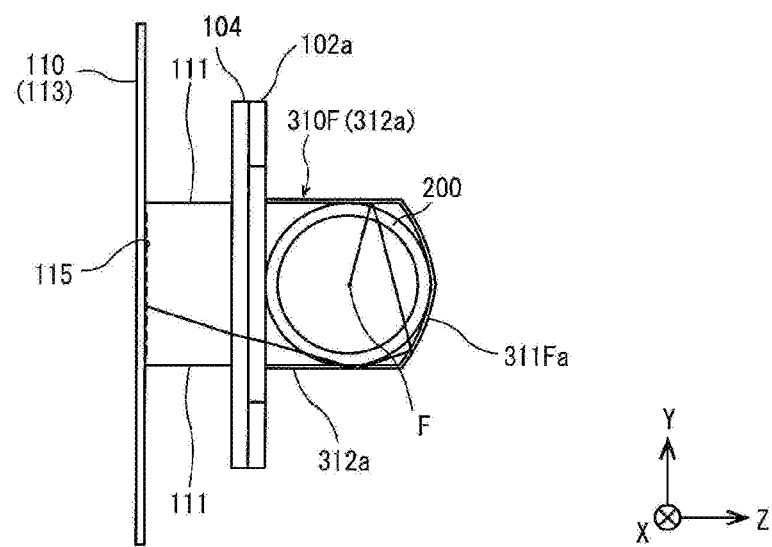
Figure 32:
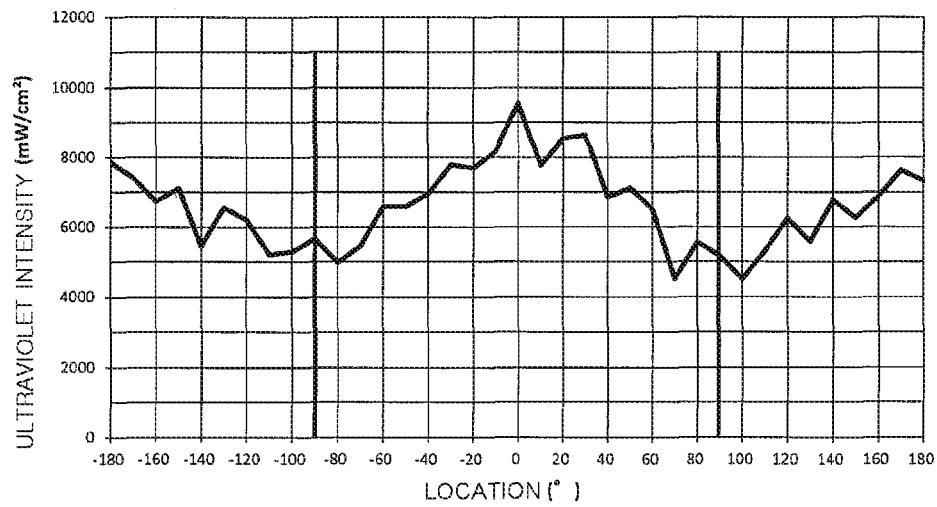
FIG. 32 is a diagram showing simulation results of ultraviolet intensity distribution on an outer peripheral surface of an optical fiber F in the case that the eighth variation of FIG. 30 is used.

FIG. 31 is a light ray diagram of ultraviolet light in the case that the reflecting mirror 310F of this variation is used, FIG. 31A is a light ray diagram showing an example of a light ray incident on a surface of the outer peripheral surface of the optical fiber F (an area of half of the outer peripheral surface disposed at the upstream side in the Z-axis direction), and FIG. 31B is a light ray diagram showing an example of a light ray incident on the other side of the outer peripheral surface of the optical fiber F (an area of half of the outer peripheral surface disposed at the downstream side in the Z-axis direction). Furthermore, FIG. 32 is a diagram showing simulation results of ultraviolet intensity distribution on the outer peripheral surface of the optical fiber F in the case that the reflecting mirror 310F of this variation is used.

As shown in FIGS. 31A and 31B, in the case that the reflecting mirror 310F of this variation is used, it is also possible to perform ultraviolet light irradiation on the entire outer peripheral surface of the optical fiber F in the same way as the sixth variation. Furthermore, as a result, as shown in FIG. 32, ranging from a surface of the outer peripheral surface of the optical fiber F (0° to −90°, 0° to 90°) to the other side (−180° to −90°, −180° to 90°), a predetermined intensity (for example, 4000 (mW/cm$^2$)) necessary to cure a coating agent coated on the outer peripheral surface of the optical fiber F is obtained. Furthermore, in this variation, a maximum value of ultraviolet intensity on the outer peripheral surface of the optical fiber F was 9547 (mW/cm²), a minimum value was 4515 (mW/cm²), and minimum value/maximum value was 47.3%.

Second Embodiment

Figure 33:
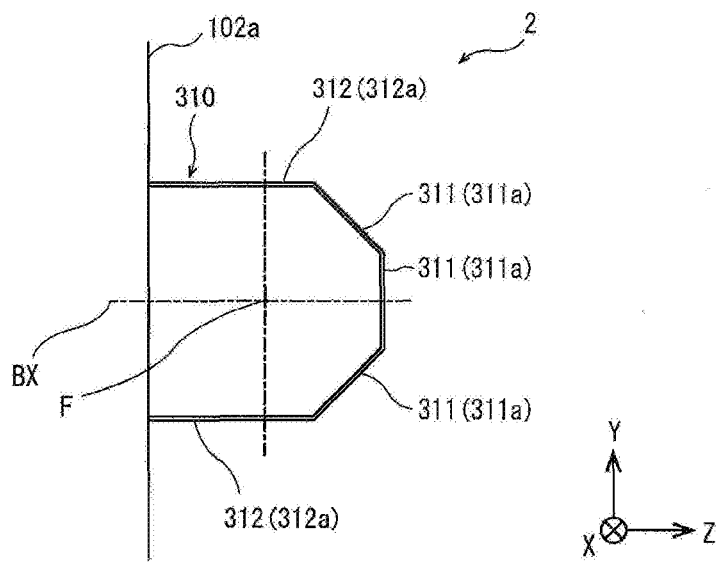
FIG. 33 is a cross-sectional view illustrating a peripheral configuration of a reflecting mirror provided in a light illuminating apparatus according to a second embodiment of the present disclosure.

FIG. 33 is a cross-sectional view illustrating a peripheral configuration of a reflecting mirror 310 of a light illuminating apparatus 2 according to a second embodiment of the present disclosure. Because the light illuminating apparatus 2 is only different from the light illuminating apparatus 1 of the first embodiment in the respect that it does not have the light transmitting pipe 200, illustration of the other elements is omitted in FIG. 33.

Figure 34A:
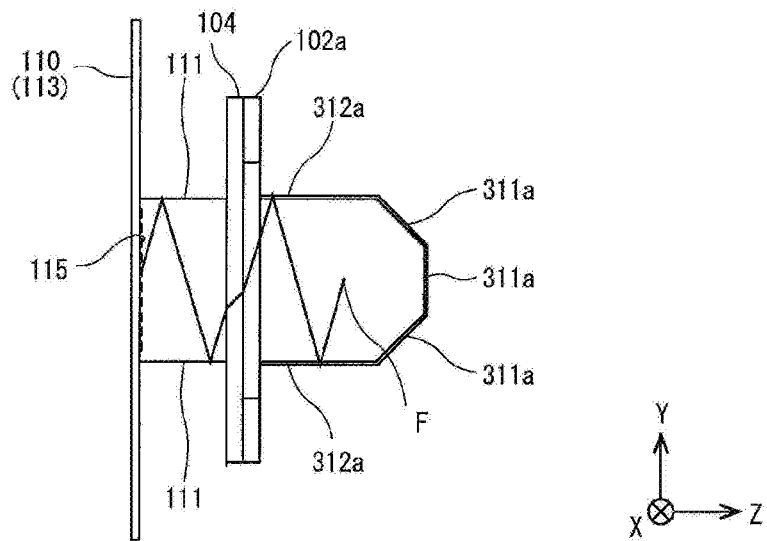
FIG. 34A and FIG. 34B are respectively a light ray diagram of ultraviolet light emitting from a light source unit of the light illuminating apparatus according to the second embodiment of the present disclosure.
Figure 34B:
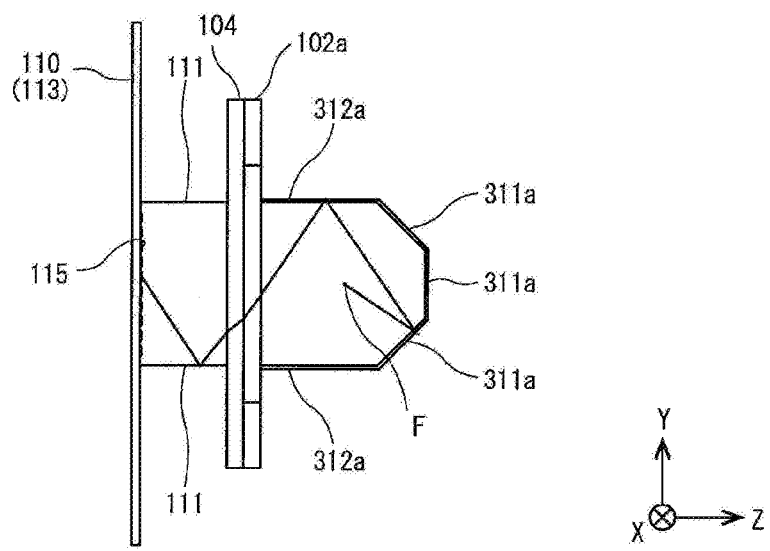
Figure 35:
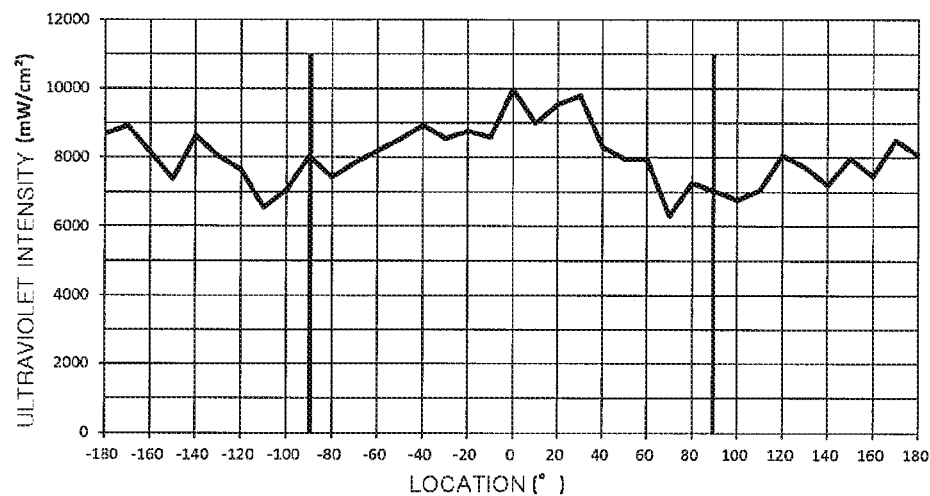
FIG. 35 is a diagram showing simulation results of ultraviolet intensity distribution on an outer peripheral surface of an optical fiber F irradiated by the light illuminating apparatus according to the second embodiment of the present disclosure.

FIG. 34 is a light ray diagram of ultraviolet light of this embodiment, FIG. 34A is a light ray diagram showing an example of a light ray incident on a surface of the outer peripheral surface of the optical fiber F (an area of half of the outer peripheral surface disposed at the upstream side in the Z-axis direction), and FIG. 34B is a light ray diagram showing an example of a light ray incident on the other side of the outer peripheral surface of the optical fiber F (an area of half of the outer peripheral surface disposed at the downstream side in the Z-axis direction). Furthermore, FIG. 35 is a diagram showing simulation results of ultraviolet intensity distribution on the outer peripheral surface of the optical fiber F of this embodiment.

As shown in FIGS. 34A and 34B, in this embodiment (namely, in the configuration with no light transmitting pipe 200), it is also possible to perform ultraviolet light irradiation on the entire outer peripheral surface of the optical fiber F in the same way as the first embodiment. Furthermore, as a result, as shown in FIG. 35, ranging from a surface of the outer peripheral surface of the optical fiber F (0° to −90°, 0° to 90°) to the other side (−180° to −90°, −180° to 90°), a predetermined intensity (for example, 6000 (mW/cm²)) necessary to cure a coating agent coated on the outer peripheral surface of the optical fiber F is obtained. Furthermore, in this embodiment, a maximum value of ultraviolet intensity on the outer peripheral surface of the optical fiber F was 9973 (mW/cm²), a minimum value was 6300 (mW/cm²), and minimum value/maximum value was 63.2%.

(Ninth Variation)

Figure 36:
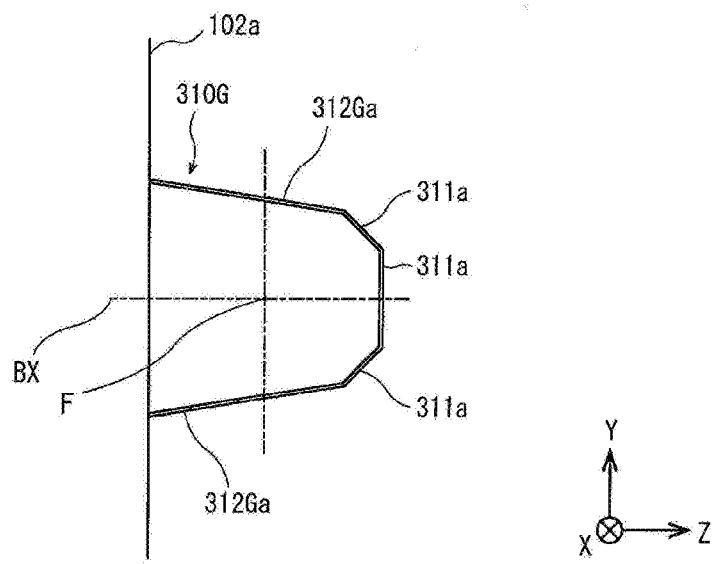
FIG. 36 is a cross-sectional view showing a ninth variation of the light illuminating apparatus according to the second embodiment of the present disclosure.

FIG. 36 is a cross-sectional view showing a ninth variation of the second embodiment of the present disclosure. A reflecting mirror 310G of this variation is configured such that a pair of second reflecting surfaces 312Ga is inclined to the straight line BX (Z-axis direction), and a spacing of the pair of second reflecting surfaces 312Ga is narrower as it goes farther from the window 104 of the light source unit 100.

Figure 37A:
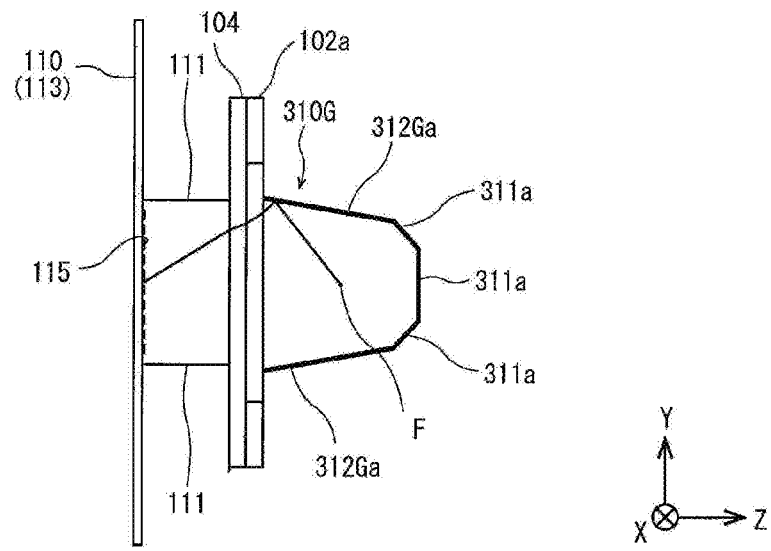
FIG. 37A and FIG. 37B are respectively a light ray diagram of ultraviolet light in the case that the ninth variation of FIG. 36 is used.
Figure 37B:
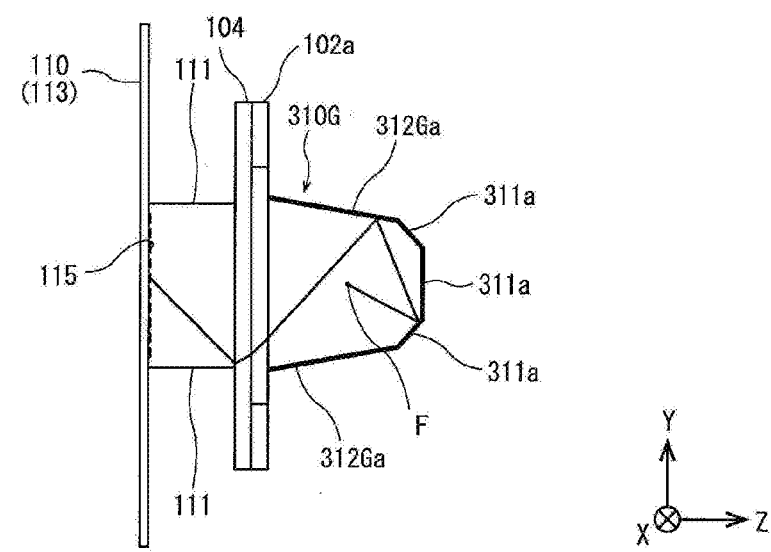
Figure 38:
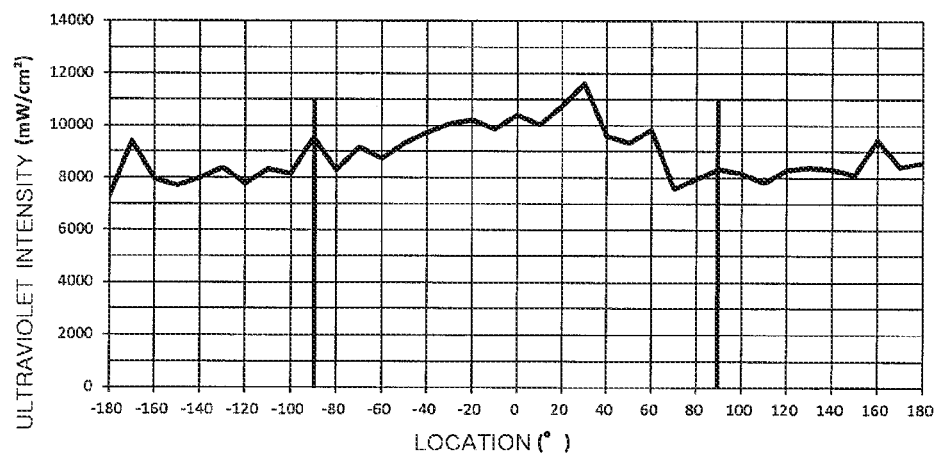
FIG. 38 is a diagram showing simulation results of ultraviolet intensity distribution on an outer peripheral surface of an optical fiber F in the case that the ninth variation of FIG. 36 is used.

FIG. 37 is a light ray diagram of ultraviolet light in the case that the reflecting mirror 310G of this variation is used, FIG. 37A is a light ray diagram showing an example of a light ray incident on a surface of the outer peripheral surface of the optical fiber F (an area of half of the outer peripheral surface disposed at the upstream side in the Z-axis direction), and FIG. 37B is a light ray diagram showing an example of a light ray incident on the other side of the outer peripheral surface of the optical fiber F (an area of half of the outer peripheral surface disposed at the downstream side in the Z-axis direction). Furthermore, FIG. 38 is a diagram showing simulation results of ultraviolet intensity distribution on the outer peripheral surface of the optical fiber F in the case that the reflecting mirror 310G of this variation is used.

As shown in FIGS. 37A and 37B, in the case that the reflecting mirror 310G of this variation is used, it is also possible to perform ultraviolet light irradiation on the entire outer peripheral surface of the optical fiber F in the same way as the second embodiment. Furthermore, as a result, as shown in FIG. 38, ranging from a surface of the outer peripheral surface of the optical fiber F (0° to −90°, 0° to 90°) to the other side (−180° to −90°, −180° to 90°), a predetermined intensity (for example, 6000 (mW/cm²)) necessary to cure a coating agent coated on the outer peripheral surface of the optical fiber F is obtained. Furthermore, in this variation, it is also possible to apply the light transmitting pipe 200 of the first embodiment. Furthermore, in this variation, a maximum value of ultraviolet intensity on the outer peripheral surface of the optical fiber F was 11607 (mW/cm²), a minimum value was 7264 (mW/cm²), and minimum value/maximum value was 62.6%.

(Tenth Variation)

Figure 39:
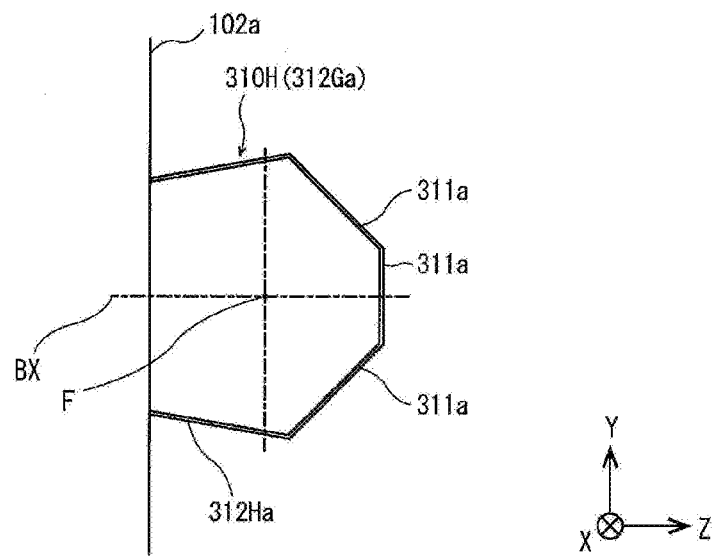
FIG. 39 is a cross-sectional view showing a tenth variation of the light illuminating apparatus according to the second embodiment of the present disclosure.

FIG. 39 is a cross-sectional view showing a tenth variation of the second embodiment of the present disclosure. A reflecting mirror 310H of this variation is configured such that a pair of second reflecting surfaces 312Ha is inclined to the straight line BX (Z-axis direction), and a spacing between the pair of second reflecting surfaces 312Ha is wider as it goes farther from the window 104 of the light source unit 100.

Figure 40A:
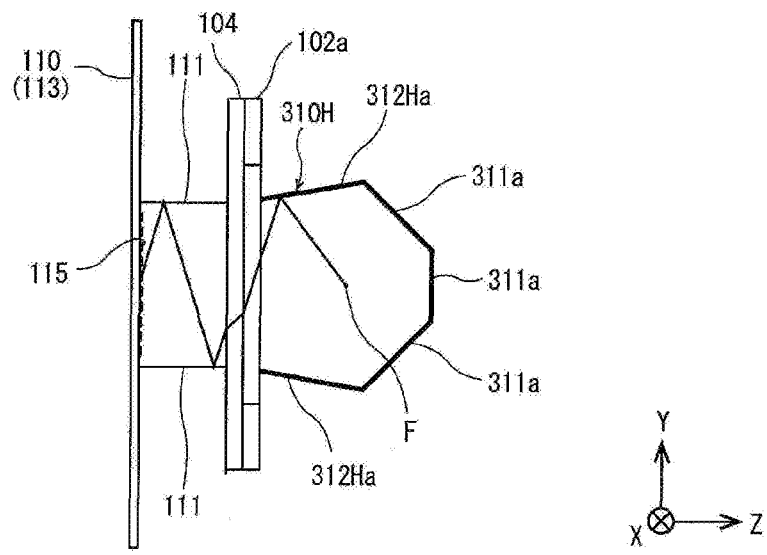
FIG. 40A and FIG. 40B are respectively a light ray diagram of ultraviolet light in the case that the tenth variation of FIG. 39 is used.
Figure 40B:
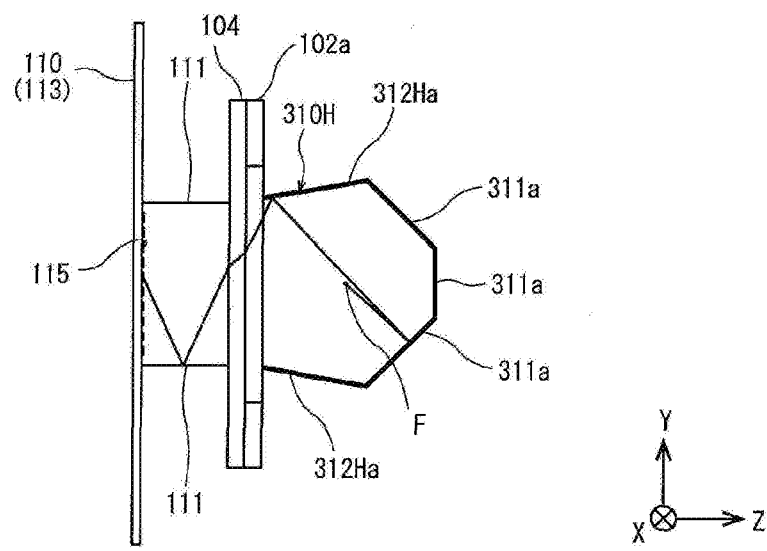
Figure 41:
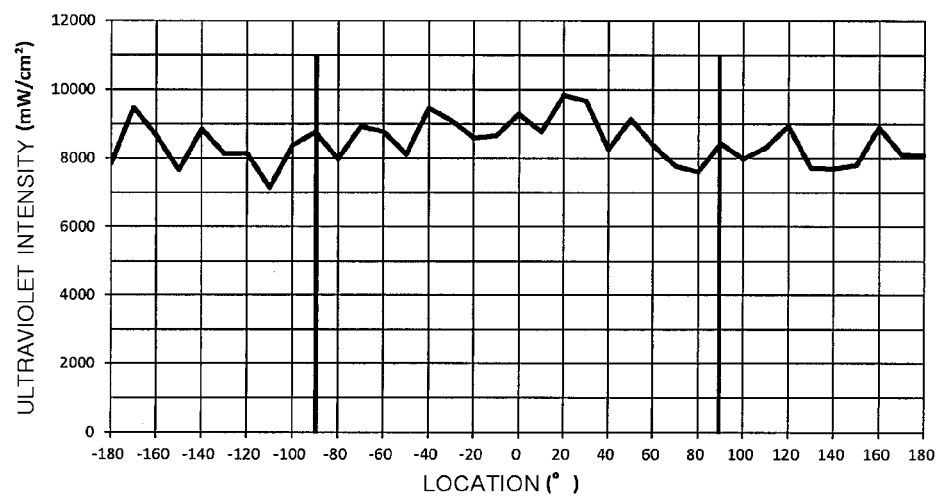
FIG. 41 is a diagram showing simulation results of ultraviolet intensity distribution on an outer peripheral surface of an optical fiber F in the case that the tenth variation of FIG. 39 is used.

FIG. 40 is a light ray diagram of ultraviolet light in the case that the reflecting mirror 310H of this variation is used, FIG. 40A is a light ray diagram showing an example of a light ray incident on a surface of the outer peripheral surface of the optical fiber F (an area of half of the outer peripheral surface disposed at the upstream side in the Z-axis direction), and FIG. 40B is a light ray diagram showing an example of a light ray incident on the other side of the outer peripheral surface of the optical fiber F (an area of half of the outer peripheral surface disposed at the downstream side in the Z-axis direction). Furthermore, FIG. 41 is a diagram showing simulation results of ultraviolet intensity distribution on the outer peripheral surface of the optical fiber F in the case that the reflecting mirror 310H of this variation is used.

As shown in FIGS. 40A and 40B, in the case that the reflecting mirror 310H of this variation is used, it is also possible to perform ultraviolet light irradiation on the entire outer peripheral surface of the optical fiber F in the same way as the second embodiment. Furthermore, as a result, as shown in FIG. 41, ranging from a surface of the outer peripheral surface of the optical fiber F (0° to −90°, 0° to 90°) to the other side (−180° to −90°, −180° to 90°), a predetermined intensity (for example, 7000 (mW/cm²)) necessary to cure a coating agent coated on the outer peripheral surface of the optical fiber F is obtained. Furthermore, in this variation, it is also possible to apply the light transmitting pipe 200 of the first embodiment. Furthermore, in this variation, a maximum value of ultraviolet intensity on the outer peripheral surface of the optical fiber F was 9833 (mW/cm²), a minimum value was 7132 (mW/cm²), and minimum value/maximum value was 72.5%.

As described in the foregoing, according to each configuration of the first embodiment, the second embodiment and the first to tenth variations of the present disclosure, it is possible to perform ultraviolet light irradiation on the entire outer peripheral surface of the optical fiber F, and obtain a predetermined intensity necessary to cure the coating agent coated on the outer peripheral surface of the optical fiber F. Furthermore, it can be seen that if the maximum intensity of ultraviolet light on the outer peripheral surface of the optical fiber F is MAX and the minimum intensity is MIN, the following equation (1) is satisfied:

$$\text{MIN}/\text{MAX} \geq 30\% \quad (1)$$

Furthermore, it should be understood that the embodiments disclosed herein are meant to be exemplary and illustrative in all aspects, not limiting in scope. The scope of the present disclosure is defined by the appended claims, not in the foregoing description, and all changes and modifications are intended to be included in the appended claims and equivalent meaning and scope.

The invention claimed is:

1. A light illuminating apparatus that irradiates a target object with light, the target object being moveable relative to the light illuminating apparatus along a first direction, the light illuminating apparatus comprising:
   a light source which irradiates the target object with the light in a second direction perpendicular to the first direction and has a plurality of solid-state devices placed on a plane defined by the first direction and a third direction perpendicular to the first direction and the second direction;
   a non-elliptical mirror module, comprising:
      a first reflecting part having at least one first reflecting surface placed at a downstream side in the second direction below the target object when viewed from the first direction, wherein the first reflecting part reflects a portion of the light from the light source incident on the first reflecting surface onto the target object; and
      a second reflecting part having a pair of second reflecting surfaces standing erect from the light source toward the first reflecting surface, wherein the second reflecting part guides the light from the light source into the first reflecting surface; and
   a pair of inner reflecting mirrors between a light source and a panel to guide the light in the second direction,
   wherein the panel is positioned between the pair of inner reflecting mirrors and the mirror module,
   wherein the mirror module is mounted on a first side of the panel and the pair of inner reflecting mirrors is mounted to a second side of the panel opposite the first side, and
   wherein the panel includes a window to allow light to pass from the light source to the mirror module.

2. The light illuminating apparatus according to claim 1, wherein the first reflecting surface has line symmetry with respect to a normal line passing through a center of the light source when viewed from the first direction.

3. The light illuminating apparatus according to claim 2, wherein the first reflecting surface includes a plurality of first reflecting surfaces each having a flat shape, and when viewed from the first direction, normal lines of at least two of the plurality of first reflecting surfaces are arranged to pass through a point on the normal line passing through the center of the light source.

4. The light illuminating apparatus according to claim 3, wherein the first reflecting surface is equivalent to a side of a polygon having an inner center on a point on the normal line passing through the center of the light source when viewed from the first direction.

5. The light illuminating apparatus according to claim 4, wherein the polygon is a polygon including a triangle up to an octadecagon.

6. The light illuminating apparatus according to claim 4, wherein the target object is placed in a space between the inner center and the first reflecting surface.

7. The light illuminating apparatus according to claim 1, wherein the first reflecting surface is in a shape of a semicircle having a center disposed on the normal line passing through the center of the light source when viewed from the first direction, and the target object is placed in a space between the center of the semicircle and the first reflecting surface.

8. The light illuminating apparatus according to claim 1, wherein the pair of second reflecting surfaces is respectively parallel to the second direction when viewed from the first direction.

9. The light illuminating apparatus according to claim 1, wherein the pair of second reflecting surfaces is inclined to the second direction when viewed from the first direction, and a spacing of the pair of second reflecting surfaces is narrower as it goes farther from the light source.

10. The light illuminating apparatus according to claim 1, wherein when a maximum intensity of the light on an outer peripheral surface of the target object is MAX and a minimum intensity is MIN, the following equation (1) is satisfied:

$$\text{MIN}/\text{MAX} \geq 30\%.$$

11. The light illuminating apparatus according to claim 1, wherein the light illuminating apparatus comprises a heat radiation member which is thermally joined to the first reflecting part and the second reflecting part, and configured to radiate heat from the first reflecting part and the second reflecting part.

12. The light illuminating apparatus according to claim 11, wherein the heat radiation member is in a shape of a plate, and has a receiving part on one side surface thereof to receive the first reflecting part and the second reflecting part.

13. The light illuminating apparatus according to claim 12, wherein the heat radiation member has a plurality of heat radiation fins on the other side surface opposite to the one side surface.

14. The light illuminating apparatus according to claim 13, wherein a cooling fan is provided to blow air to the heat radiation fins.

15. The light illuminating apparatus according to claim 1, wherein the light illuminating apparatus further comprises a light transmitting pipe installed extending in the first direction to cover the target object, the light transmitting pipe through which the light from the light source transmits.

16. The light illuminating apparatus according to claim 1, wherein the light is light in ultraviolet wavelength range.

17. The light illuminating apparatus according to claim 16, wherein the target object has a shape of a line, a sphere or a particle, and the light in ultraviolet wavelength range cures a coating agent coated on the outer peripheral surface of the target object.

18. The light illuminating apparatus according to claim 16, wherein the target object is in liquid phase, and the light in ultraviolet wavelength range sterilizes the target object.

19. The light illuminating apparatus according to claim 5, wherein the target object is placed in a space between the inner center and the first reflecting surface.

20. The light illuminating apparatus according to claim 2, wherein the first reflecting surface is in a shape of a semicircle having a center disposed on the normal line passing through the center of the light source when viewed from the first direction, and the target object is placed in a space between the center of the semicircle and the first reflecting surface.

* * * * *